(12) United States Patent
Walker et al.

(10) Patent No.: US 9,631,235 B2
(45) Date of Patent: Apr. 25, 2017

(54) MITOCHONDRIAL NUCLEIC ACID AS A MARKER FOR AUTOIMMUNE AND AUTOINFLAMMATORY DISEASES

(75) Inventors: Ulrich Walker, Freiburg (DE); Dirk Lebrecht, Frieburg (DE); Nils Venhoff, Freiburg (DE)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

(21) Appl. No.: 14/114,733

(22) PCT Filed: Apr. 30, 2012

(86) PCT No.: PCT/EP2012/057919
§ 371 (c)(1),
(2), (4) Date: Nov. 26, 2013

(87) PCT Pub. No.: WO2012/146783
PCT Pub. Date: Nov. 1, 2012

(65) Prior Publication Data
US 2014/0099648 A1    Apr. 10, 2014

(30) Foreign Application Priority Data

Apr. 29, 2011 (EP) .................................... 11164329

(51) Int. Cl.
C12Q 1/68 (2006.01)
(52) U.S. Cl.
CPC ...... *C12Q 1/6883* (2013.01); *C12Q 2600/118* (2013.01); *C12Q 2600/158* (2013.01)
(58) Field of Classification Search
None
See application file for complete search history.

(56) References Cited

FOREIGN PATENT DOCUMENTS

| EP | 0 812 922 A2 | 12/1997 |
|---|---|---|
| EP | 0812922 A2 * | 12/1997 |
| EP | 1 538 218 A1 | 6/2005 |
| WO | WO 03/095674 | 11/2003 |
| WO | WO 2007/106790 A1 | 9/2007 |

OTHER PUBLICATIONS

Feng et al. (Diagnostic potential of mitochondrial DNA assessment in patients with optic neuropathy, Chin Med J (Engl). Aug. 2000;113(8):743-6).*
Su et al. (The role of extracellular DNA in autoimmunity in SLE, Scand J Immunol. Sep. 2009;70(3):175-83).*
Chiu et al. (Quantitative Analysis of Circulating Mitochondrial DNA in Plasma, Clin Chem. May 2003;49(5):719-26).*
Zhang et al. (Circulating mitochondrial DAMPs cause inflammatory responses to injury, Nature. Mar. 4, 2010;464(7285):104-7).*
Swarup et al. (Circulating (cell-free) nucleic acids—A promising, non-invasive tool for early detection of several human diseases, FEBS Lett. Mar. 6, 2007;581(5):795-9. Epub Feb. 2, 2007).*
Jonsen et al. (Mitochondrial DNA polymorphisms are associated with susceptibility and phenotype of systemic lupus erythematosus, Lupus. Apr. 2009;18(4):309-12).*
Vyshkina et al. (Association of common mitochondrial DNA variants with multiple sclerosis and systemic lupus erythematosus, Clin Immunol. Oct. 2008;129(1):31-5. Epub Aug. 16, 2008).*
Salmon et al. (The role of apoptosis in systemic lupus erythematosus, Rheumatology (1999) 38 (12): 1177-1183, Jul. 2009).*
Galeazzi et al. (Dosage and characterization of circulating DNA: present usage and possible applications in systemic autoimmune disorders, Autoimmun Rev. Jan. 2003;2(1):50-5).*
Fernandez et al. (Metabolic control of T cell activation and death in SLE, Autoimmun Rev. Jan. 2009;8(3):184-9. Epub Aug. 21, 2008).*
Lee et al. (Underexpression of mitochondrial-DNA encoded ATP synthesis-related genes and DNA repair genes in systemic lupus erythematosus, Arthritis Res Ther. Apr. 15, 2011;13(2):R63).*
Collins et al. (Endogenously oxidized mitochondrial DNA induces in vivo and in vitro inflammatory responses, J Leukoc Biol. Jun. 2004;75(6):995-1000. Epub Feb. 24, 2004).*
Hajizadeh et al. (Extracellular mitochondrial DNA and oxidatively damaged DNA in synovial fluid of patients with rheumatoid arthritis, Arthritis Res Ther, 2003, 5:R234, Jun. 25, 2003).*
Krysko et al. (Emerging role of damage-associated molecular patterns derived from mitochondria in inflammation, Trends Immunol. Apr. 2011;32(4):157-64. Epub Feb. 19, 2011).*
Setzer et al. (Effects of of didanosine-related depletion of mtDNA in human T lymphocytes, J Infect Dis. Mar. 15, 2005;191(6):848-55. Epub Feb. 10, 2005).*
Zhang, Qin et al., "Circulating mitochondrial DAMPs cause inflammatory responses to injury", Nature, vol. 464, No. 7265, pp. 104-107 (Mar. 2010).
Khurana Rahul et al., "Mitochondrial oxidative DNA damage in experimental autoimmune uveitis", IOVS, vol. 49, No. 8, pp. 3299-3304 (Aug. 2008).
Yu, X et al., "Association of UCP2-866 G/A polymorphism with chronic inflammatory diseases", Genes and Immunity, vol. 10, No. 6, pp. 601-605 (Sep. 2009).
Feng X et al., "Diagnostic potential of mitochondrial DNA assessment in patients with optic neuropathy", Chinese Medical Journal, vol. 113, No. 8, pp. 743-746 (Aug. 2000).
Gene L. Davis et al., "Detection of Circulating DNA by Counterimmunoelectrophoresis (CIE)", Arthritis and Rheumatism, vol. 16, No. 1, pp. 52-58 (Jan.-Feb. 1973).
Haiting Wang et al., "Neutrophil Extracellular Trap Mitochondril DNA and Its Autoantibody in Systemic Lupus Erythematosus and a Proof-of-Concept Trial of Metformin", *Arthritis & Rheumatology*, vol. 67, No. 12, Dec. 2015, pp. 3190-200.
M.P. Surmiak et al., "Circulating Mitochondrial DNA in Serum of Patients with Granulomatosis with Polyangiitis", Clinical & Experimental Immunology, vol. 181, Mar. 2015, pp. 150-155.

* cited by examiner

*Primary Examiner* — Aaron Priest
(74) *Attorney, Agent, or Firm* — Chalin A. Smith; Smith Patent, LLC

(57) ABSTRACT

The present invention relates to a method for increasing the diagnostic likelihood of the presence or absence of, or monitoring the progression or activity of an inflammatory autoimmune disease (AID), comprising detecting mitochondrial NA (e.g. mtDNA) in a sample from an individual suffering from the AID or suspected of suffering from the AID.

6 Claims, 10 Drawing Sheets

Figure 1:
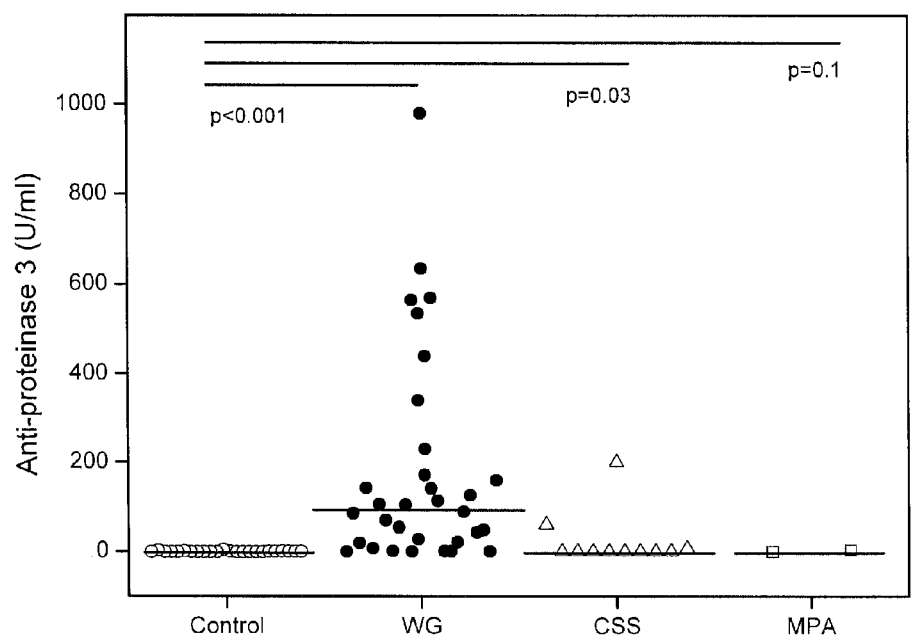

MITOCHONDRIAL NUCLEIC ACID AS A MARKER FOR AUTOIMMUNE AND AUTOINFLAMMATORY DISEASES

This application corresponds to the national phase of International Application No. PCT/EP2012/057919 filed Apr. 30, 2012 which, in turn, claims priority to European Patent Application No. 11.164329.2 filed Apr. 29, 2011, the contents of which are incorporated by reference herein in their entirety.

The instant application contains a Sequence Listing that has been submitted in ASCII format via EFS-Web and is hereby incorporated by reference in its entirety. Said ASCII copy, created on Oct. 29, 2013, is named LNK_141_SequenceListing.txt and is 938 bytes in size.

The present invention concerns the diagnosis of autoimmune and autoinflammatory diseases, called AID.

BACKGROUND OF THE INVENTION

Polymorphonuclear neutrophils recognize conserved structures in microbial pathogens, referred to as pathogen-associated molecular patterns (PAMPs) by means of toll like receptors (TLRs), rendering them important players in the innate immune system[1]. Among the TLRs, TLR9 signaling has been implicated in the pathogenesis of lupus and other 'autoimmune' diseases[2,3]. TLR9 is exclusively expressed in intracellular vesicles and recognizes unmethylated Cytosine-phosphatidyl-Guanine (CpG) DNA motifs that are frequently present in bacteria and viruses, but are rare in mammalian cells[1]. TLR ligand binding activates the regulatory transcription factor nuclear factor-κB and induces the secretion of pro-inflammatory cytokines.

Trauma and other forms of cellular injury can release endogenous 'damage'-associated molecular patterns (DAMPs) that, similar to microbial PAMPs, also activate innate immunity[4]. Upon such injury, cells can release mitochondrial DNA (mtDNA) which contains unmethylated CpG motifs and resembles bacterial DNA[1]. MtDNA in clinically relevant concentrations has been shown to activate human polymorphonuclear neutrophils through TLR9, a process which promotes their degranulation, and elicits systemic inflammation and organ injury including inflammatory lung injury[4].

A recently discovered aspect of the antimicrobial defense of polymorphonuclear leukocytes is their ability to release chromatin in the form of extracellular fibers called neutrophil extracellular traps (NETs)[5-7]. It has been demonstrated in eosinophils that the process of NET formation is an early event of cell death called 'NETosis'. Polymorphonuclear neutrophils and eosinophils play an important role in the pathogenesis of ANCA-associated vasculitis (AAV), such as Wegener's granulomatosis (WG), microscopic polyangiitis (MPA) and Churg-Strauss syndrome (CSS). These forms of vasculitis are associated with the presence of antineutrophil cytoplasmatic antibodies (ANCA) in the serum of affected patients[8]. It has been demonstrated that in WG, ANCA are mostly directed against proteinase 3 (PR3), whereas in MPA ANCA tend to be directed against myeloperoxidase. PR3-ANCA may have a direct pathogenic role in the pathogenesis of WG by activating primed neutrophils and also by inducing endothelial cell damage[8].

It has been recently demonstrated that endothelial cell activation elicits NET formation and that conversely NETs can induce endothelial cell injury[9]. Thus NETs may also play an important role in the pathogenesis of AAV. In this context it is also interesting to note that the propensity for disease relapses in WG may be enhanced by bacterial infections with *Staphylococcus aureus*[10-12], which are also known to trigger NET formation[13]. Finally, it has been shown that not only bacterial stimuli such as *S. aureus*, but also ANCA are able to induce NETosis[14]. Indeed PR3 and myeloperoxidase have been found in physical association with NET components in the glomeruli of individuals with ANCA-associated glomerulonephritis[14].

A problem of the present invention is to provide a suitable marker useful in supporting or decreasing the likelihood of the diagnosis of AID in clinically unclear situations. Another problem of the present invention is to provide a marker of disease activity that could be useful in determining the intensity of the therapy of said AID.

The inventors surprisingly found that patients suffering from AID show elevated levels of mitochondrial DNA circulating in plasma. Furthermore, the ratio of mitochondrial DNA to nuclear DNA was elevated. The invention therefore pertains to the diagnosis of AID by determining the amount of mitochondrial nucleic acids and/or the ratio of mitochondrial to nuclear nucleic acids, and to other aspects associated therewith.

Zhang et al. (2010) Nature 464, 104-108 describes experiments suggesting that circulating mitochondrial 'damage'-associated molecular patterns (DAMPs) cause inflammatory responses to injury. Zhang et al. does not disclose the diagnosis of autoimmune and autoinflammatory diseases (AID).

Khurana et al. (2008) Invest. Ophthalmol. Vis. Sci. 49, 3299-3304 investigates whether oxidative mitochondrial DNA damage occurs early in experimental autoimmune uveitis (EAU), before leukocyte infiltration. Damage to mitochondrial DNA and nuclear DNA was assessed using a long quantitative polymerase chain reaction technique. Khurana et al. does not disclose the diagnosis of autoimmune and autoinflammatory diseases (AID) nor does it suggest that elevated levels of mitochondrial DNA in plasma could be indicative of AID.

Yu et al. (2009) Genes and Immunity 10, 601-605 reports an association of a certain mitochondrial gene polymorphism (UCP2-866 G/A) with chronic inflammatory diseases. Yu et al. does not determine the amount or concentration of circulating mitochondrial DNA in samples of patients. Rather, the disclosure of Yu et al. is limited to genotyping of the polymorphism.

Feng et al. (2000) Chinese Medical Journal 113(8), 743-746 investigates the primary mutations of mitochondrial DNA associated with Leber's hereditary optic neuropathy (LHON) in patients with optic neuropathy. Feng et al. does not determine the amount or concentration of circulating mitochondrial DNA in patient samples. Rather, Feng et al. detects certain mutations in mitochondrial genes.

WO 2007/106790 A2 describes methods, compositions and uses thereof, relating to vitiligo or vitiligo-associated autoimmune/autoinflammatory disease (VAAAD). In particular embodiments, genetic variations in the NALP1 gene are of use to detect, diagnose, predict the risk of or treat at least one of vitiligo or VAAAD. In more particular embodiments, the presence of genetic variations such as single-nucleotide polymorphisms (SNPs) in NALP1 genetic region are of use to detect, diagnose or predict the risk of VAAAD. In other embodiments, inhibitors targeted to NALP1, caspase-1 or caspase-5, ASC (PYCARD), interleukin-1ss, interleukin-1ss receptor, or interleukin 18 may be administered to a subject to treat VAAAD. The gene NALP1 is a chromosomal gene, and, therefore, WO 2007/106790 A2 does not aim at determining the amount of mitochondrial DNA.

EP 812922 A2 describes novel human mitochondrial polymorphisms, and probes and primers for detecting the same. Detection of such polymorphisms is said to be useful in a variety of fields such as forensic analysis, epidemiology and preventive medicine. This reference does not determine the amount or concentration of circulating mitochondrial DNA in patient samples. Rather, the disclosure of EP 812922 A2 et al. is limited to genotyping of the polymorphisms.

EP 1538218 A1 describes methods to diagnose or screen for inflammatory condition or disease, including auto-inflammatory disease and affective disorder, in a subject, preferably a human subject, by assaying for a marker for an inflammatory disease. Described is a method to diagnose or screen for an inflammatory disease in a subject, said method comprising determining the level of various inflammatory-specific gene product(s) in a biological sample isolated from said subject, preferably peripheral blood monocytes, wherein said inflammatory-specific gene is selected from the group comprising HSPC228, 34703_f_at, MCP-3, CCL2, EMP1, CDC42, TLE3, SPRY2, p40BBP, HSPC060, NAB2, HSPA1A, HSPA1B, MAPRE2, OAS1, CCR2, CX3CR1, DOK1, HBB, G-gamma globin, THBD, PHLDA1, DTR and GNLY. EP 1538218 A1 neither teaches nor suggests determining the amount of mitochondrial DNA.

SUMMARY OF THE INVENTION

In a first aspect, the present invention relates to a method for diagnosing an autoimmune or autoinflammatory disease (AID), comprising detecting mitochondrial nucleic acid (mtNA) in a sample from an individual suffering from the AID or suspected of suffering from the AID.

In a second aspect, the present invention relates to a method for ruling out an autoimmune or autoinflammatory disease (AID), comprising detecting mitochondrial nucleic acid (mtNA) in a sample from an individual suspected of suffering from the AID.

In a third aspect, the present invention relates to a method for monitoring the progression and/or activity of an autoimmune or autoinflammatory disease (AID), comprising detecting mitochondrial nucleic acid (mtNA) in a sample from an individual suffering from the AID or suspected of suffering from the AID over a period of time.

In another aspect, the present invention relates to the use of mitochondrial NA (e.g. mtDNA) as a marker for inflammatory autoimmune disease. Preferably, the mitochondrial NA is used as a laboratory marker for AID.

In yet another aspect, the present invention relates to the use of a primer pair for diagnosing, ruling out AID, or monitoring the activity of AID, wherein said primer pair is capable of specifically amplifying mtNA in a polymerase chain reaction.

In yet another aspect, the invention relates to a diagnostic kit for diagnosing or monitoring the progression of AID, comprising (1) at least one pair of oligonucleotide primers capable of specifically amplifying mtNA in a polymerase chain reaction, (2) at least one oligonucleotide capable of specifically hybridizing with mtNA, (3) a compound, preferably an antibody, specifically recognizing mtNA, or (4) an enzyme specifically recognizing mtNA.

The invention further relates to a screening method for identifying compounds effective in the treatment of AID, comprising
(a) contacting a test compound with a cell; and
(b) determining the amount of mtNA released by said cell.

For all aspects of the present invention the mtNA may be mitochondrial DNA (mtDNA) or mitochondrial RNA (mtRNA). Preferably, the mtNA is mtDNA.

DETAILED DESCRIPTION

The present invention relates to a method for diagnosing or monitoring the progression or activity of an autoimmune or autoinflammatory disease.

Autoimmune or Autoinflammatory Disease

Autoimmune and autoinflammatory diseases (AID) are disorders characterized by an aberrant response of the acquired or innate immune system, resulting in a destruction of its own cells or tissues. Preferably, the disease to be diagnosed or monitored in accordance with the present invention are AID associated with, but not restricted to, systemic, e.g. multiorgan inflammation. In the present application, an AID is considered inflammatory if it shows signs of inflammation, by either an increased level of C-reactive protein (CRP), or an abnormal infiltrate of inflammatory cells in the affected tissues on histology or cytology at some stage during the course of the disease. In a particular embodiment, the AID is a systemic AID. An AID is considered systemic if it does not only concern specific organs or tissues, but affects multiple organs or tissues. In some cases, the effects of the disease can be found ubiquitously in an organism.

Preferably, the AID to be diagnosed and/or monitored according to this invention is selected from the group consisting of ANCA-associated vasculitis (AAV), connective tissues diseases (systemic lupus erythematosus (SLE), systemic sclerosis, polymyositis, dermatomyositis, Sjögren's syndrome, undifferentiated and overlap forms), inflammatory bowel diseases (such as colitis ulcerosa and Crohn's disease), crystal arthropathies (such as gout, pseudogout, and hydroxyapatite deposition disease), different forms of arthritis (e.g. rheumatoid arthritis, juvenile arthritis, psoriatic arthritis and the spondylarthropathies), psoriasis and sarcoidosis and the adult-respiratory distress syndrome (ARDS), as well as Familial Mediterranean Fever, autoinflammatory periodic fever syndromes (e.g. the cryopyrin associated fever syndromes, and others), or adult onset Still's disease. Further AIDs include all types of large or medium sized vessel inflammations (vasculitides) for example giant cell arteriitis (GCA), aortitis, Behcet's disease, as well as polymyalgia rheumatica. The AAV may be Wegener's granulomatosis (WG), microscopic polyangiitis (MPA), Churg-Strauss syndrome (CSS) or isolated ANCA-associated glomerulonephritis. Other AID in which mtNA testing has diagnostic utility according to this invention are all types of large vessel vasculitides for example giant cell arteriitis (GCA), aortitis, Behcet's disease, as well as polymyalgia rheumatica and different forms of arthritis either involving the axial skeleton or peripheral joints (such as the spondylarthropathies, rheumatoid arthritis and psoriatic arthritis). Finally, the Adult Respiratory Distress Syndrome, psoriatic skin disease, sarcoidosis, Familial Mediterranean Fever, autoinflammatory periodic fever syndromes (e.g. the cryopyrin associated fever syndromes, and others), Adult onset Still's disease is also considered as an AID in terms of our invention.

Further the AID may be active AID or inactive AID. Preferably, the AID is active AID, more preferably the AID is active AAV, an active connective tissue disease (such as SLE, systemic sclerosis, myositis, Sjögren's syndrome, overlap or undifferentiated forms), an active crystal arthropathy (such as gout, pseudogout or hydroxyapatite deposition disease), as well as an active inflammatory bowel disease (such as colitis ulcerosa or Crohn's disease). Other preferred AID according to this invention are active forms of the following disorders: all types of large and medium sized vessel inflammations (vasculitides) for example giant cell arteriitis (GCA), aortitis, Behcet's disease, as well as polymyalgia rheumatica and arthritis involving the axial skeleton and/or peripheral joints (such as the spondylarthropathies, rheumatoid arthritis and psoriatic arthritis); the Adult Respiratory Distress Syndrome, psoriatic skin disease, Familial Mediterranean Fever, autoinflammatory periodic fever syndromes (e.g. the cryopyrin associated fever syndromes, and others). Adult Still's disease and sarcoidosis can be also considered as an AID.

Sample

In one embodiment, the method of the invention comprises detecting mtNA (e.g. mtDNA or mtRNA) in the sample.

The term "sample" as used herein designates a composition which is derived from the body fluid of an individual. Body fluids include blood, urine, milk, cerebrospinal fluid, cell-free bronchial lavage and the like. Preferred samples are compositions comprising blood, plasma or serum obtained or derived from the individual. The sample may be a composition which has been processed to be in a condition suitable for the method according to the invention. The processing may include centrifugation, absorption, immunocapture, extraction, precipitation, concentration, filtration, dialysis and/or dilution. The type of processing may depend on the technique which is used for detecting the mitochondrial nucleic acid in the sample. For example, a blood sample may be subject to centrifugation such that plasma is obtained. In another embodiment, the sample may be diluted prior to analysis. In yet another embodiment, DNA or RNA is extracted from a blood or plasma sample prior to analysis. In a preferred embodiment, a blood sample obtained from the individual is first centrifuged to obtain plasma, and total DNA is then extracted from said plasma. The sample obtained in this way may then be analysed further.

In one embodiment, the method of the invention comprises only steps which are carried out in vitro. In that embodiment, the step of obtaining the sample from the body of the individual is not encompassed by the present invention. In another embodiment, the step of obtaining the sample from the body of the individual is encompassed by the present invention.

Detecting mtNA

The mtNA to be detected may be mitochondrial DNA (mtDNA) or mitochondrial RNA (mtRNA). Preferably, the mtNA is mtDNA. Preferably, the mtNA to be detected is circulating mtNA. "Circulating" nucleic acid is cell-free nucleic acid which can be found in a body fluid of an individual, e.g. in blood and/or urine.

The step of detecting mtNA in the sample may include determining the presence or absence of mtNA in the sample in a qualitative manner. Preferably, however, the step of detecting mtNA includes determining the amount or concentration of mtNA in the sample in a quantitative or semi-quantitative manner. Most preferably, the step of detecting mtNA includes determining the amount or concentration of mtDNA in the sample in a quantitative manner.

The method of the invention preferably comprises detection of the mtNA by way of polymerase chain reaction (PCR). The method of the invention can include PCR assays, such as qualitative, semi-quantitative or quantitative PCR or RT-PCR, optionally involving a coamplification of a mitochondrial sequence and a reference sequence, such as a nuclear sequence. The method of the invention may also include hybridization assays, for example, RNA or DNA hybridization assays, using mitochondrial and nuclear DNA or RNA samples in mitochondrial and reference sequences as probes. The method of the invention may also include quantification methods utilizing antibodies directed against mtNA sequences, dyes or other labels intercalating into or absorbing onto mtNA or nuclear DNA or RNA. Information from such assays can be evaluated to provide a ratio of mitochondrial nucleic acid to nuclear nucleic acid (mtDNA to nuclear DNA or mtRNA to nuclear RNA) in the cells or tissues of the individual. The method may further comprise detecting nuclear nucleic acid (nNA), e.g. nDNA or nRNA in the sample. Preferably, the method comprises determining the copy number of mtDNA in the individual. This can be done by determining the amount of mtDNA in the sample and calculating the copy number as shown in the examples.

In alternative embodiments, the change of relative mitochondrial nucleic acid (e.g. mtDNA or mtRNA) concentration over a time period may also be determined to provide diagnostic information. In alternative embodiments, the invention also provides protocols that, for example, avoid the necessity to determine mtDNA copy number per se, facilitating instead a determination of the relative amount of mitochondrial nucleic acid, e.g. the amount relative to nuclear nucleic acid.

Methods of quantitative PCR are for example disclosed in the following documents, all of which are incorporated herein by reference: U.S. Pat. No. 6,180,349; U.S. Pat. No. 6,033,854; and U.S. Pat. No. 5,972,602; Song, J. et al. (2001) Diabetes Care 24:865-869. A mitochondrial DNA or RNA sequence may be chosen from any mitochondrion-specific nucleotide sequence, including but not limited to ATP synthase 6, GenBank Accession No. AF368271; tRNA-Leu, GenBank Accession No. S49541; NADH dehydrogenase subunit 5 (MTND5), GenBank Accession No. AF339085; cytochrome b, GenBank Accession No. AF254896, or any other suitable any mitochondrion-specific nucleotide sequence. A nuclear DNA or RNA sequence may be chosen from any sequence, including but not limited to a human GAPDH sequence, a human 28S rRNA sequence, a beta-globin sequence, or any other suitable nuclear DNA or RNA sequence. Amplification probes may be designed according to methods known in the art and described, for example, in Sambrook, et al. (Molecular Cloning: A Laboratory Manual. $3^{rd}$ ed., Cold Spring Harbor Laboratory, Cold Spring Harbor Laboratory Press, Cold Spring Harbor, N.Y., 2001) or Ausubel et al. (Current Protocols in Molecular Biology, John Wiley & Sons, 1994).

Preferably, the method comprises amplifying DNA of the mitochondrial ATP-6 gene. Optionally, the method further comprises amplifying DNA of the nuclear GAPDH gene.

Alternatively, hybridization techniques may be employed to determine the presence or amount of mtNA in the sample. Suitable techniques using oligonucleotides or polynucleotides under stringent conditions are known to the skilled person. Preferably, the oligonucleotides or polynucleotides used as probes specifically hybridize with mtNA sequences (see above).

The presence or amount of mtNA may further be determined by using polypeptides or carbohydrate ligands specifically recognizing mtNA, e.g. mtDNA. For example, antibodies recognizing hypomethylated DNA can be used in immunological assays that are known per se such as an ELISA. Alternatively, TLR9 may be used in a typical binding assay as polypeptide capable of binding to mtDNA.

In other embodiments, an enzyme may be used which specifically targets hypomethylated DNA. For example, the enzyme may specifically cut hypomethylated DNA. At such "nick" sites a non radioactive label (e.g. biotin) or a radiolabel could be attached. Such label can then be quantified.

In another embodiment, mtNA may first be isolated specifically from a pool of different nucleic acids and contaminants, for example by means of density gradient centrifugation. In a second step mtNA may then be quantified with any unspecific nucleic acid quantification method.

Diagnosis

The method for diagnosing an autoimmune or autoinflammatory disease (AID) may comprise the following steps:

obtaining and/or collecting a sample from a patient;

detecting circulating mtNA in the sample from the patient, preferably determining the amount or concentration of circulating mtNA in the sample;

comparing the amount or concentration of mtNA detected in the sample with a standard amount or concentration of mtNA found in healthy individuals (see infra);

diagnosing AID if the amount or concentration of the mtNA detected in the sample from the patient is greater than the standard amount or concentration of mtNA found in healthy individuals, and optionally if one or more other established criteria of AID are fulfilled, see infra.

The average amount of mtDNA in the plasma of healthy individuals is about 10,000 to about 32,000 copies per ml plasma. The average amount of mtDNA in individuals affected by an AID usually is about 250,000 to about 1,200,000 copies per ml plasma.

In one aspect of the invention the detection of an elevated level of mtDNA in the sample from the individual relative to control samples increases the probability of the presence of the AID in a given population. In another important aspect of the invention, the detection of normal levels of mtDNA lowers the probability of the presence of an AID in a given population, or even excludes the diagnosis. Likewise, the extent of elevation of mtDNA in the sample from the individual relative to control samples may correlate to the activity of the AID in the individual.

The control samples have been obtained from individuals not suffering from AID or other causes of systemic inflammation, preferably from healthy individuals. Concentrations of mtDNA in the plasma >50,000 copies per ml plasma are typically associated with the presence of AID. Accordingly, the individual may be more likely to suffer from the AID or as having the AID or as being affected by the AID if the amount of mtDNA in the plasma of the individual is greater than 30,000 copies per ml plasma, preferably if the amount of mtDNA in the plasma of the individual is greater than 50,000 copies per ml plasma, more preferably if the amount of mtDNA in the plasma of the individual is greater than 150,000 copies per ml plasma. Conversely, an active AID can be ruled out with high confidence in an individual with 15,000 or less mtDNA copies per ml plasma.

In another embodiment, the individual may be diagnosed as suffering from the AID or as having the AID or as being affected by the AID if the amount of mtDNA in the plasma of the individual exceeds the median mtDNA copy number in control plasma from healthy individuals by at least 50%, preferably be at least 100%, more preferably by at least 200%, still more preferably by at least 500%, most preferably by at least 1,000%.

In yet another embodiment, the individual may be diagnosed as suffering from the AID or as having the AID or as being affected by the AID if the mtDNA/nDNA ratio in the plasma from the individual is greater than 5, preferably greater than 10, more preferably greater than 20, most preferably greater than 30.

In yet another embodiment, the individual may be diagnosed as suffering from the AID or as having the AID or as being affected by the AID if the mtDNA/nDNA ratio in the plasma from the individual exceeds the median mtDNA/nDNA ratio in control individuals by at least 100%, preferably be at least 200%, more preferably be at least 300%, most preferably by at least 500%.

In particular embodiments, the individual is diagnosed as suffering from the AID or as having the AID or as being affected by the AID if (1) any one of the above criteria relating to mtNA and (2) one or more of the established criteria for the diagnosis and/or classification of the respective AID is/are satisfied. The individual may be diagnosed as suffering from the AID or as having the AID or as being affected by the AID if (1) any one of the above criteria relating to mtNA and (2) at least one of the established criteria for the diagnosis and/or classification of the respective AID is satisfied. In another embodiment, the individual is diagnosed as suffering from the AID or as having the AID or as being affected by the AID if (1) any one of the above criteria relating to mtNA and (2) two or more of the established criteria for the diagnosis and/or classification of the respective AID are satisfied. In yet another embodiment, the individual is diagnosed as suffering from the AID or as having the AID or as being affected by the AID if (1) any one of the above criteria relating to mtNA and (2) three or more of the established criteria for the diagnosis and/or classification of the respective AID are satisfied. In yet another embodiment, the individual is diagnosed as suffering from the AID or as having the AID or as being affected by the AID if (1) any one of the above criteria relating to mtNA and (2) four or more of the established criteria for the diagnosis and/or classification of the respective AID are satisfied. In yet another embodiment, the individual is diagnosed as suffering from the AID or as having the AID or as being affected by the AID if (1) any one of the above criteria relating to mtNA and (2) five or more (e.g. six, seven, eight, nine or ten) of the established criteria for the diagnosis and/or classification of the respective AID are satisfied.

The established criteria for the diagnosis and/or classification of AID depend on which specific AID is concerned. In the following we summarize the so far established criteria for several AIDs (1 to 19):

1. 1987 American College of Rheumatology Revised Classification Criteria for Rheumatoid Arthritis

| Criterion | Description |
|---|---|
| Morning stiffness | Morning stiffness in and around the joints, lasting at least one hour before maximal improvement. |
| Arthritis of 3 or more joint areas | At least 3 joint areas (out of 14 possible areas; right or left PIP, MCP, wrist, elbow, knee, ankle, MTP joints) simultaneously have had soft-tissue swelling or fluid (not bony overgrowth alone) as observed by a physician. |

| Criterion | Description |
|---|---|
| Arthritis of hand joints | At least one area swollen (as defined above) in a wrist, MCP, or PIP joint. |
| Symmetric arthritis | Simultaneous involvement of the same joint areas (as defined above) on both sides of the body (bilateral involvement of PIPs, MCPs, or MTPs, without absolute symmetry is acceptable). |
| Rheumatoid nodules | Subcutaneous nodules over bony prominences or extensor surfaces, or in juxta-articular regions as observed by a physician. |
| Serum rheumatoid factor | Demonstration of abnormal amounts of serum rheumatoid factor by any method for which the result has been positive in less than 5 percent of normal control subjects. |
| Radiographic changes | Radiographic changes typical of rheumatoid arthritis on posteroanterior hand or wrist radiographs, which must include erosions or unequivocal bony decalcification localised in, or most marked adjacent to, the involved joints (osteoarthritis changes alone do not qualify). |

Note: For classification purposes, a patient has RA if at least four of these criteria are satisfied (the first four must have been present for at least six weeks).

Reference:

Arnett F C, Edworthy S M, Bloch D A, McShane D J, Fries J F, Cooper N S, Healey L A, Kaplan S R, Liang M H, Luthra H S. The American Rheumatism Association 1987 revised criteria for the classification of rheumatoid arthritis. Arthritis Rheum. 1988; 31(3):315.

2. The 2010 ACR-EULAR Classification Criteria for Rheumatoid Arthritis

| | Score |
|---|---|
| Target population (Who should be tested?): Patients who have at least 1 joint with definite clinical synovitis (swelling) * with the synovitis not better explained by another disease Classification criteria for RA (score-based algorithm: add score of categories A-D; a score of ≥6/10 is needed for classification of a patient as having definite RA) ‡ | |
| A. Joint involvement § | |
| 1 large joint ¶ | 0 |
| 2-10 large joints | 1 |
| 1-3 small joints (with or without involvement of large joints) # | 2 |
| 4-10 small joints (with or without involvement of large joints) | 3 |
| >10 joints (at least 1 small joint)** | 5 |
| B. Serology (at least 1 test result is needed for classification) †† | |
| Negative RF and negative ACPA | 0 |
| Low-positive RF or low-positive ACPA | 2 |
| High-positive RF or high-positive ACPA | 3 |
| C. Acute-phase reactants (at least 1 test result is needed for classification)‡‡ | |
| Normal CRP and normal ESR | 0 |
| Abnormal CRP or abnormal ESR | 1 |
| D. Duration of symptoms §§ | |
| <6 weeks | 0 |
| ≥6 weeks | 1 |

* The criteria are aimed at classification of newly presenting patients. In addition, patients with erosive disease typical of rheumatoid arthritis (RA) with a history compatible with prior fulfillment of the 2010 criteria should be classified as having RA. Patients with longstanding disease, including those whose disease is inactive (with or without treatment) who, based on retrospectively available data, have previously fulfilled the 2010 criteria should be classified as having RA.
‡ Although patients with a score of <6/10 are not classifiable as having RA, their status can be reassessed and the criteria might be fulfilled cumulatively over time.
§ Joint involvement refers to any swollen or tender joint on examination, which may be confirmed by imaging evidence of synovitis. Distal interphalangeal joints, first carpometacarpal joints, and first metatarsophalangeal joints are excluded from assessment. Categories of joint distribution are classified according to the location and number of involved joints, with placement into the highest category possible based on the pattern of joint involvement.
¶ "Large joints" refers to shoulders, elbows, hips, knees, and ankles.
"Small joints" refers to the metacarpophalangeal joints, proximal interphalangeal joints, second through fifth metatarsophalangeal joints, thumb interphalangeal joints, and wrists.
** In this category, at least 1 of the involved joints must be a small joint; the other joints can include any combination of large and additional small joints, as well as other joints not specifically listed elsewhere (e.g., temporomandibular, acromioclavicular, sternoclavicular, etc.).
†† Negative refers to IU values that are less than or equal to the upper limit of normal (ULN) for the laboratory and assay; low-positive refers to IU values that are higher than the ULN but ≤3 times the ULN for the laboratory and assay; high-positive refers to IU values that are >3 times the ULN for the laboratory and assay. Where rheumatoid factor (RF) information is only available as positive or negative, a positive result should be scored as low-positive for RF. ACPA = anti-citrullinated protein antibody.
‡‡ Normal/abnormal is determined by local laboratory standards. CRP = C-reactive protein; ESR = erythrocyte sedimentation rate.
§§ Duration of symptoms refers to patient self-report of the duration of signs or symptoms of synovitis (e.g., pain, swelling, tenderness) of joints that are clinically involved at the time of assessment, regardless of treatment status.

References:

Aletaha D, Neogi T, Silman A J, Funovits J, Felson D T, Bingham C O 3rd, Birnbaum N S, Burmester G R, Bykerk V P, Cohen M D, Combe B, Costenbader K H, Dougados M, Emery P, Ferraccioli G, Hazes J M, Hobbs K, Huizinga T W, Kavanaugh A, Kay J, Kvien T K, Laing T, Mease P, Ménard H A, Moreland L W, Naden R L, Pincus T, Smolen J S, Stanislawska-Biernat E, Symmons D, Tak P P, Upchurch K S, Vencovsky J, Wolfe F, Hawker G. 2010 rheumatoid arthritis classification criteria: an American College of Rheumatology/European League Against Rheumatism collaborative initiative. Ann Rheum Dis. 2010; 69(9):1580.

Aletaha D, Neogi T, Silman A J, Funovits J, Felson D T, Bingham C O 3rd, Birnbaum N S, Burmester G R, Bykerk V P, Cohen M D, Combe B, Costenbader K H, Dougados M, Emery P, Ferraccioli G, Hazes J M, Hobbs K, Huizinga T W, Kavanaugh A, Kay J, Kvien T K, Laing T, Mease P, Ménard H A, Moreland L W, Naden R L, Pincus T, Smolen J S, Stanislawska-Biernat E, Symmons D, Tak P P, Upchurch K S, Vencovsky J, Wolfe F, Hawker G. 2010 Rheumatoid arthritis classification criteria: an American College of Rheumatology/European League Against Rheumatism collaborative initiative. Arthritis Rheum. 2010; 62(9):2569.

3. Classification Criteria Psoriasis Arthritis (CASPAR Study Group 2006)

Presence of musculoskeletal inflammation (an inflammatory arthritis, enthesitis, or back pain);

PLUS three points from the following:

Skin psoriasis (present) (two points), previously present by history (one point), or a family history of psoriasis (one point) if the patient is not affected Nail lesions (onycholysis, pitting)—one point Dactylitis (present or past, documented by a rheumatologist)—one point Negative rheumatoid factor—one point Juxtaarticular bone formation on radiographs (distinct from osteophytes)—one point Reference:

Taylor W, Gladman D, Helliwell P, Marchesoni A, Mease P, Mielants H, CASPAR Study Group. Classification criteria for psoriatic arthritis: development of new criteria from a large international study. Arthritis Rheum. 2006; 54(8): 2665.

4. ACR Criteria for Diagnosis of Systemic Lupus Erythematosus (1982)

| Criterion | Definition |
|---|---|
| 1. Malar rash | Fixed erythema, flat or raised, over the malar eminences, tending to spare the nasolabial folds |
| 2. Discoid rash | Erythematous raised patches with adherent keratotic scaling and follicular plugging; atrophic scarring may occur in older lesions |
| 3. Photosensitivity | Skin rash as a result of unusual reaction to sunlight, by patient history or physician observation |
| 4. Oral ulcers | Oral or nasopharyngeal ulceration, usually painless, observed by a physician |
| 5. Arthritis | Nonerosive arthritis involving 2 or more peripheral joints, characterized by tenderness, swelling, or effusion |
| 6. Serositis | Pleuritis - convincing history of pleuritic pain or rub heard by a physician or evidence of pleural effusion OR Pericarditis - documented by EKG, rub or evidence of pericardial effusion |
| 7. Renal disorder | Persistent proteinuria greater than 0.5 grams per day or greater than 3+ if quantitation not performed OR Cellular casts - may be red cell, hemoglobin, granular, tubular, or mixed |
| 8. Neurologic disorder | Seizures OR psychosis - in the absence of offending drugs or known metabolic derangements (uremia, ketoacidosis, or electrolyte imbalance) |
| 9. Hematologic disorder | Hemolytic anemia - with reticulocytosis OR Leukopenia - less than 4,000/mm3 total on two or more occasions OR Lymphopenia - less than 1,500/mm3 on two or more occasions OR Thrombocytopenia - less than 100,000/mm3 in the absence of offending drugs |
| 10. Immunologic disorders | Positive antiphospholipid antibody OR Anti-DNA - antibody to native DNA in abnormal titer OR Anti-Sm - presence of antibody to Sm nuclear antigen OR False positive serologic test for syphilis known to be positive for at least six months and confirmed by Treponema pallidum immobilization or fluorescent treponemal antibody absorption test |
| 11. Antinuclear antibody | An abnormal titer of antinuclear antibody by immunofluorescence or an equivalent assay at any point in time and in the absence of drugs known to be associated with "drug-induced lupus" syndrome |

The proposed classification is based on 11 criteria. For the purpose of identifying patients in clinical studies, a person shall be said to have systemic lupus erythematosus if any 4 or more of the 11 criteria are present, serially or simultaneously, during any interval of observation.

Reference:

Tan E M, Cohen A S, Fries J F, Masi A T, McShane D J, Rothfield N F, Schaller J G, Talal N, Winchester R J. The 1982 revised criteria for the classification of systemic lupus erythematosus. Arthritis Rheum. 1982; 25(11):1271.

5. The American College of Rheumatology 1990 Criteria for the Classification of Wegener's Granulomatosis

| Criterion | Definition |
|---|---|
| Nasal or oral inflammation | Development of painful or painless oral ulcers or purulent or bloody nasal discharge |
| Abnormal chest radiograph | Chest radiograph showing the presence nodules, fixed infiltrates, or cavities |
| Urinary sediment | Microhematuria (>5 red blood cells per high power field) or red cell casts in urine sediment |
| Granulomatous inflammation on biopsy | Histologic changes showing granulomatous inflammation within the wall of an artery or in the perivascular or extravascular area (artery or arteriole) |

The presence of two or more of these four criteria yielded a sensitivity of 88 percent and a specificity of 92 percent Reference:

Leavitt R Y, Fauci A S, Bloch D A, Michel B A, Hunder G G, Arend W P, Calabrese L H, Fries J F, Lie J T, Lightfoot R W Jr. The American College of Rheumatology 1990 criteria for the classification of Wegener's granulomatosis. Arthritis Rheum. 1990; 33(8):1101.

6. ACR Classification Criteria Churg-Strauss Syndrome (1990)

| Criteria and definitions used for the classification of Churg-Strauss syndrome | |
|---|---|
| Asthma | History of wheezing or diffuse high-pitched rales on expiration y |
| Eosinophilia | Eosinophilia >lo % on white blood cell differential count |
| History of allergy* | History of seasonal allergy (e.g., allergic rhinitis) or other documented allergies, including food, contactants, and others, exceptfor drug allerg |
| Mononeuropathy or polyneuropathy | Development of mononeuropathy, multiple rnononeuropathies, or polyneuropathy (i.e., glovelstocking distribution) attributable to a systemic vasculitis |
| Pulmonary infiltrates, non-fixed | Migratory or transitory pulmonary infiltrates on radiographs (not including fixed infiltrates), attributable to a systemic vasculitis |
| Paranasal sinus abnormality | History of acute or chronic paranasal sinus pain or tenderness or radiographic opacification of the paranasal sinuses |
| Extravascular eosinophils | Biopsy including artery, arteriole, or venule, showing accumulations of eosinophils in extravascular areas |

*History of allergy, other than asthma or drug-related, is included only in the tree classification criteria set and not in the traditional format criteria set, which requires 4 or more of the 6 other items listed here.

Reference:

Masi A T, Hunder G G, Lie J T, Michel B A, Bloch D A, Arend W P, Calabrese L H, Edworthy S M, Fauci A S, Leavitt R Y. The American College of Rheumatology 1990 criteria for the classification of Churg-Strauss syndrome (allergic granulomatosis and angiitis). Arthritis Rheum. 1990; 33(8):1094.

7. Micoscopic Polyangiitis no classification criteria

Chapel Hill Consensus Conference on the Nomenclature of Systemic Vasculitis

Names and Definitions of Vasculitides Adopted by the Chapel Hill Consensus Conference on the Nomenclature of Systemic Vasculitis*

Names and definitions of vasculitides adopted by the Chapel Hill Consensus Conference on the Nomenclature of Systemic Vasculitis*

Large vessel vasculitis

| | |
|---|---|
| Giant cell (temporal) arteritis | Granulomatous arteritis of the aorta and its major branches, with a predilection for the extracranial branches of the carotid artery. Often involves the temporal artery. Usually occurs in patients older than 50 and often is associated with polymyalgia rheumatica. |
| Takayasu arteritis | Granulomatous inflammation of the aorta and its major branches. Usually occurs in patients younger than 50. |

Medium-sized vessel vasculitis

| | |
|---|---|
| Polyarteritis nodosa (classic polyarteritis nodosa) | Necrotizing inflammation of medium-sized or small arteries without glomerulonephritis or vasculitis in arterioles, capillaries, or venules. |
| Kawasaki disease | Arteritis involving large, medium-sized, and small arteries, and associated with mucocutaneous lymph node syndrome. Coronary arteries are often involved. Aorta and veins may be involved. Usually occurs in children. |

Small vessel vasculitis

| | |
|---|---|
| Wegener's granulomatosis ‡ | Granulomatous inflammation involving the respiratory tract, and necrotizing vasculitis affecting small to medium-sized vessels (e.g., capillaries, venules, arterioles, and arteries). Necrotizing glomerulonephritis is common. |
| Churg-Strauss syndrome ‡ | Eosinophil-rich and granulomatous inflammation involving the respiratory tract, and necrotizing vasculitis atrecting small to medium-sized vessels, and associated with asthma and eosinophilia. |
| Microscopic polyangiitis † (microscopic polyarteritis) ‡ | Necrotizing vasculitis, with few or no immune deposits, affecting small vessels (i.e., capillaries, venules, or arterioles). Necrotizing arteritis involving small and medium- sized arteries may be present. Necrotizing glomerulonephritis is very common. Pulmonary capillaritis often occurs. |
| Henoch-Schonlein purpura | Vasculitis, with IgA-dominant immune deposits, affecting small vessels (i.e., capillaries, venules, or arterioles). Typically involves skin, gut, and glomeruli, and is associated with arthralgias or arthritis. |
| Essential cryoglobulinemic vasculitis | Vasculitis, with cryoglobulin immune deposits, affecting small vessels (i.e., capillaries, venules, or arterioles), and associated with cryoglobulins in serum. Skin and glomeruli are often involved. |
| Cutaneous leukocytoclastic angiitis | Isolated cutaneous leukocytoclastic angiitis without systemic vasculitis or glomerulonephritis. |

*Large vessel refers to the aorta and the largest branches directed toward major body regions (e.g., to the extremities and the head and neck); medium-sized vessel refers to the main visceral arteries (e.g., renal, hepatic, coronary, and mesenteric arteries); small vessel refers to venules, capillaries, arterioles, and the intraparenchymal distal arterial radicals that connect with arterioles. Some small and large vessel vasculitides may involve medium-sized arteries, but large and medium-sized vessel vasculitides do not involve vessels smaller than arteries. Essential components are represented by normal type; italicized type represents usual, but not essential, components,
† Preferred term.
‡ Strongly associated with antineutrophil cytoplasmic autoantibodies.

Reference:

Jennette J C, Falk R J, Andrassy K, Bacon P A, Churg J, Gross W L, Hagen E C, Hoffman G S, Hunder G G, Kallenberg C G. Nomenclature of systemic vasculitides. Proposal of an international consensus conference. Arthritis Rheum. 1994; 37(2):187.

8. Diagnostic Criteria for Behcet's Disease, International Study Group for Behcet's Disease 1990

| Criterion | Required features |
|---|---|
| Recurrent oral ulceration Plus any two of the following: | Minor aphthous, major aphthous, or herpetiform ulceration observed by physician or patient, which recurred at least 3 times in one 12-month period |
| Recurrent genital ulceration | Aphthous ulceration or scarring, observed by physician or patient |
| Eye lesions | Anterior uveitis, posterior uveitis, or cells in vitreous on slit lamp examination; or Retinal vasculitis observed by ophthalmologist |
| Skin lesions | Erythema nodosum observed by physician or patient, pseudofolliculitis, or papulopustular lesions; or Acneiform nodules observed by physician in postadolescent patients not on corticosteroid treatment |
| Positive pathergy test | Read by physician at 24-48 h. |

Findings applicable only in absence of other clinical explanations.

Reference:

Criteria for diagnosis of Behçet's disease. International Study Group for Behçet's Disease. Lancet. 1990; 335(8697): 1078.

9. Sarcoidosis

A definitive diagnostic test for sarcoidosis does not exist. The diagnosis of sarcoidosis requires three elements:

Compatible clinical and radiographic manifestations

Exclusion of other diseases that may present similarly

Histopathologic detection of noncaseating granulomas

Reference:

Statement on sarcoidosis. Joint Statement of the American Thoracic Society (ATS), the European Respiratory Society (ERS) and the World Association of Sarcoidosis and Other Granulomatous Disorders (WASOG) adopted by the ATS Board of Directors and by the ERS Executive Committee, February 1999. Am J Respir Crit Care Med 1999; 160:736.

10. Ulcerative Colitis

"The diagnosis of ulcerative colitis can usually be established by the characteristic history coupled with a typical endoscopic appearance of the mucosa and confirmatory histology seen on colonic biopsy. CT scan may also show marked thickening of the bowel wall, but this finding is nonspecific. A helpful historical clue is the presence of ulcerative colitis in first-degree relatives." (UpToDate 19.1)

11. Crohn's Disease

"The diagnosis of Crohn's disease is usually established with endoscopic findings or imaging studies in a patient with a compatible clinical history. Physical examination may be normal or show nonspecific signs (pallor, weight loss) suggestive of Crohn's disease. More specific findings include perianal skin tags, sinus tracts, and abdominal tenderness. Presenting symptoms frequently determine the order of subsequent testing. Colonoscopy is the most appropriate initial test for patients presenting with predominant diarrhea, while imaging studies may be more appropriate for those presenting with abdominal pain." (UpToDate 19.1)

12. Preliminary ARA-Criteria for the Classification of Systemic Sclerosis (Scleroderma)

| Criterion | Definition |
| --- | --- |
| major criterion or two or more of the following: | proximal scleroderma |
| minor criteria | 1) sclerodactyly<br>2) digital pitting scars of fingertips or loss of substance of the distal finger pad<br>3) bilateral basilar pulmonary fibrosis |

The proposed criteria had a 97% sensitivity for definite systemic sclerosis and 98% specificity.

Glossary of Clinical Terms used in Description or Classification of Systemic Sclerosis 1. Typical sclerodermatous skin changes: tightness, thickening, and non-pitting induration, excluding the localized forms of scleroderma (morphea or linear scleroderma)
   a. Sclerodactyly: above-indicated changes limited to (fingers and toes)
   b. Proximal scleroderma: above-indicated changes proximal to the metacarpophalangeal or metatarsophalangeal joints, affecting other parts of the extremities, face, neck, or trunk (thorax or abdomen); usually bilateral, symmetrical and almost always including sclerodactyly
2. Other skin manifestations attributable to systemic sclerosis or comparison disorders
   a. Digital pitting scars or loss of substance from the finger pad: depressed areas at tips of digits or loss of digital pad tissue as a result of digital ischemia rather than trauma or exogenous causes
   b. Bilateral finger or hand edema: firm but pitting edema, especially involving fingers (includes puffy sausage-like swelling of fingers) or the dorsal aspect of the hands
   c. Abnormal skin pigmentation: hyperpigmentation often containing areas of punctate or patchy hypopigmentation or depigmentation ("pepper and salt")
   d. Raynaud's phenomenon: at least two-phase color change in fingers and often toes consisting of pallor, cyanosis, and/or reactive hyperemia in response to cold exposure or emotion, as determined by patient's history or physician's observation
3. Visceral manifestations
   a. Bibasilar pulmonary fibrosis: bilateral reticular pattern of linear or lineonodular densities which are most pronounced in basilar portions of the lungs on standard chest roentgenogram; may assume appearance of diffuse mottling or "honeycomb lung," and should not be attributable to primary lung disease
   b. Lower (distal) esophageal dysphagia: substernal discomfort on swallowing or sensation of food holdup in the retrosternal location
   c. Lower (distal) esophageal dysmotility: hypoperistalsis or aperistalsis, as demonstrated by either cine esophagram or fluoroscopy or by manometric study, often accompanied by evidence of decrease in lower esophageal sphincter tone with reflux of gastric contents into the esophagus
   d. Colonic sacculations: wide-mouthed diverticula of colon located along the antimesenteric border; found on barium enema examination; these sacculations may also occur in ileum and jejunum Reference:
Masi A T, et al. Preliminary criteria for the classification of systemic sclerosis (scleroderma). Subcommittee for scleroderma criteria of the American Rheumatism Association Diagnostic and Therapeutic Criteria Committee. Arthritis Rheum. 1980 May; 23(5):581-90.

13. Criteria for the Classification of the Acute Arthritis of Primary Gout
   1. Monosodium urate monohydrate microcrystals in joint fluid during attack
   2. More than one attack of acute arthritis
   3. Maximum inflammation developed within 1 day
   4. Monoarthritis attack
   5. Redness observed over joints
   6. First metatarsophalangeal joint painful or swollen
   7. Unilateral first metatarsophalangeal joint attack
   8. Unilateral tarsal joint attack
   9. Tophus (proven or suspected)
   10. Hyperuricemia
   11. Asymmetric swelling within a joint on x ray
   12. Subcortical cysts without erosions on x ray
   13. Joint fluid culture negative for organisms during attack The combination of crystals, tophi, and/or 6 or more criteria is highly suggestive of gout.

Reference:
Wallace S L, Robinson H, Masi A T, Decker J L, McCarty D J, Yü T F. Preliminary criteria for the classification of the acute arthritis of primary gout. Arthritis Rheum. 1977 April; 20(3):895-900.

14. "Diagnostic Criteria and Diagnostic Classification for Calcium Pyrophosphate Dihydrate (CPPD) Crystal Deposition Disease A definite diagnosis of CPPD crystal deposition disease requires either:
   The demonstration of CPPD crystals in tissue or synovial fluid by definitive means (eg, x-ray diffraction, etc) OR
   The presence of both positively (but weakly) birefringent crystals by compensated polarized light microscopy and typical cartilage or joint capsule calcification on x-ray examination In current clinical practice, definitive demonstration of crystals by x-ray diffraction powder pattern, chemical analysis, or atomic force microscopy is only rarely achieved except in specialized centers of research. Thus, the diagnosis is most commonly established by fulfilling the combination of radiographic and synovial fluid analysis criteria.

A probable diagnosis of CPPD crystal deposition disease occurs with either:
   The identification of positively (but weakly) birefringent crystals by compensated polarized light microscopy OR
   The presence of typical cartilage or joint capsule calcification on radiographic examination.

The majority of patients considered to have CPPD crystal deposition disease by rheumatologists most likely fall into the probable disease category. Given the current state of management of this disorder, this fact does not appear to be a serious diagnostic quandary if alternative diagnostic possibilities are carefully considered and appropriately acted upon.

Fulfillment of either of the following criteria should raise the suspicion of possible CPPD crystal deposition disease and prompt a direct evaluation aimed at fulfilling specific criteria for the disorder:
   Acute arthritis of large joints, especially the knees OR
   Chronic arthritis which resembles osteoarthritis, particularly if the involved joints are not typical for osteoarthritis (wrists, MCP joints, elbows, and shoulders) and if accompanied by acute, self-limited attacks. As previously mentioned, distinction from osteoarthritis is further suggested by radiographic features typical of CPPD arthropathy in individual joints and the spine (even in the absence of chondrocalcinosis); severe and progressive joint degeneration, especially with prominent subchondral cyst formation; and tendon calcifications apparent on radiographs.

The criteria for possible CPPD crystal deposition disease are aimed at calling attention to the possibility of the disorder and stimulating the search for more definitive criteria. They are not intended to attach a diagnostic label to an individual patient." UpToDate 19.1

References:

Rosenthal, A K, Ryan, L M, McCarty, D J. Calcium pyrophosphate crystal deposition disease, pseudogout, and articular chondrocalcinosis. In: Arthritis and Allied Conditions, 15th ed, Koopman, W J, Moreland, L W (Eds), Lippincott Williams & Wilkins, Philadelphia, 2005, p. 2373.

Rosenthal, A K. Pseudogout: presentation, natural history, and associated conditions. In: Crystal-induced Arthropathies. Gout, Pseudogout and Apatite-associated Syndromes, Wortmann, R L, Schumacher, H R Jr, Becker, M A, Ryan, L M (Eds), Taylor & Francis Group, New York, 2006. p. 99.

15. The American College of Rheumatology 1990 Criteria for the Classification of Giant Cell Arteritis.

| Criterion | Definition |
| --- | --- |
| 1. Age at disease onset >=50 years | Development of symptoms or findings beginning at age 50 or older |
| 2. New headache | New onset of or new type of localized pain in the head |
| 3. Temporal artery abnormality | Temporal artery tenderness to palpation or decreased pulsation, unrelatd to arteriosclerosis of cervical arteries |
| 4. Elevated erythrocyte sedimentation rate | Erythrocyte sedimentation rate >=50 mm/hour by the Westergren method |
| 5. Abnormal artery biopsy | Biopsy specimen with artery showing vasculitis characterized by a predominance of mononuclear cell infiltration or granulomatous inflammation, usually with multinucleated giant cells |

* For purposes of classification, a patient shall be said to have giant cell (temporal) arteritis if at least 3 of these 5 criteria are present. The presence of any 3 or more criteria yields a sensitivity of 93.5% and a specificity of 91.2%

Reference:

Hunder G G, Bloch D A, Michel B A, Stevens M B, Arend W P, Calabrese L H, Edworthy S M, Fauci A S, Leavitt R Y, Lie J T, et al. The American College of Rheumatology 1990 criteria for the classification of giant cell arteritis. Arthritis Rheum. 1990 August; 33(8):1122-8.

16. Criteria for Polymyalgia Rheumatica (PMR).

| Criterion |
| --- |
| Shoulder pain and/or stiffness bilaterally |
| Onset of illness of <2 weeks duration |
| Initial ESR >40 mm/h |
| Morning stiffness duration >1 h |
| Age >65 years |
| Depression and/or loss of weight |
| Upper arm tenderness bilaterally |

A patient might be regarded as having probable PMR if any 3 or more of these criteria are fulfilled, or if at least 1 criterion coexists with a clinical or pathological abnormality of the temporal artery.

Reference:

Bird H A, Esselinckx W, Dixon A S, Mowat A G, Wood P H. An evaluation of criteria for polymyalgia rheumatica. Ann Rheum Dis. 1979 October; 38(5):434-9.

17. Classification Criteria for Dermatomyositis and Polymyositis (1975)

| Criterion |
| --- |
| 1. Symmetric proximal muscle weakness |
| 2. Elevation of serum levels of skeletal muscle enzymes including creatine kinase (CK), aldolase, aspartate aminotransferase (AST), alanine aminotransferase (ALT) and lactate dehydrogenase (LH) |
| 3. Abnormal Electromyography (EMG) with myopathic motor unit potentials, fibrillations, positive sharp waves and increased insertional irritability. |
| 4. Muscle biopsy features of inflammatory infiltration and either degeneration/regeneration or perifascicular atrophy. |
| 5. Typical skin rash of Dermatomyositis, that includes Gottron's sign, Gottron's papules or heliotrope rash |

Definite polymyositis: criteria 1-4; probable polymyositis: three of criteria 1-4; possible polymyositis: two of criteria 1-4; definite dermatomyositis: criterion 5 and three of criteria 1-4; probable dermatomyositis: criterion 5 and two of criteria 1-4; possible dermatomyositis: criterion 5 and one of criteria 1-4.
The application of these criteria assumes that known infectious, toxic, metabolic, dystrophic or endocrine myopathies have been excluded by appropriate evaluations.
Symmetry is intended to denote bilateral but not necessarily equal involvement.

Reference:

1. Bohan A, Peter J B. Polymyositis and dermatomyositis (first of two parts). N Engl J Med. 1975; 292:344-7.
2. Bohan A, Peter J B. Polymyositis and dermatomyositis (second of two parts). N Engl J Med. 1975; 292:403-7.

18. Criteria for the Diagnosis of Familial Mediterranean Fever (FMF).

| Major criteria |
| --- |
| Typical attacks |
| 1. Peritonitis (generalised) |
| 2. Pleuritis (unilateral) or pericarditis |
| 3. Monoarthritis (hip, knee, ankle) |
| Minor criteria |
| 1-3. Incompete attacks involving one or more of the following sites: |
| 1. Abdomen |
| 2. Chest |
| 3. Joint |
| 4. Exertional leg pain |
| 5. Favourable response to colchicine |
| Supportive criteria |
| 1. Family history of FMF |
| 2. Appropriate ethnic origin |
| 3. Age less than 20 years at disease onset |
| 4.-6. Features of attacks: 4. Severe, requiring bed rest; 5. Spontaneous remission; 6. Symptom-free interval |
| 7. Transient inflammatory response, with one or more abnormal test result(s) for white blood cell count, erythrocyte sedimentation rate, serum amyloid A and/or fibrinogen |
| 8. Episodic proteinuria/haematuria |
| 9. Unproductive laparotomy or removal of "white" appendix |
| 10. Consanguinity of parents |

The requirements for the diagnosis of FMF are one or more major criteria, or two or more minor criteria, or one minor plus five or more supportive criteria, or one minor criterion plus four or more of the first five supportive criteria. Typical attacks are defined as recurrent (three or more of the same type), febrile (rectal temperature of 38° C. or higher) and short (lasting between 12 h and 3 days). Incomplete attacks are defined as painful and recurrent attacks that differ from typical attacks in one or two features as follows: the temperature is normal or lower than 38° C.; the attacks are longer or shorter than specified (but no shorter than 6 h or longer than a week); no signs of peritonitis are recorded during the abdominal attacks; the abdominal attacks are localised; the arthritis is in joints other than those specified. Attacks are not counted if they do not fit the definition of either typical or incomplete attacks.

Reference:

Livneh A, Langevitz P, Zemer D, Zaks N, Kees S, Lidar T, Migdal A, Padeh S, Pras M. Criteria for the diagnosis of familial Mediterranean fever. Arthritis Rheum. 1997 October; 40(10):1879-85.

19. Classification of the Autoinflammatory Periodic Fever Syndromes

| Diseases | Gene/chromosome | Protein | Clinical features |
|---|---|---|---|
| Periodic/recurrent fevers | | | |
| Familial Mediterranean fever (FMF) | MEVF 16p13.3 | Pyrin | see above |
| Mevalonate deficiency | MVK 12q24 | Mevalonatkinase | early onset (usually <12 months); mean duration of fever episodes 4-5 days. Poor conditions during fever episodes. Abdominal pain, vomiting and diarrhoea. Splenomegaly. Good response to steroids. High rate of self-resolution during adulthood. Amyloidosis is rare. |
| TNF receptor associated periodic syndrome | TNFRSF1A 12p13 | P55 TNF receptor | Prolonged fever episodes 1-3 weeks. Periorbital oedema, monocytic fasciitis. Incidence of renal amyloidosis. Response to TNF and IL1 blockade. |
| NALP12-associated periodic fever | NALP12 | NALP12 | Periodic fever after cold exposure, hearing loss |
| Cryopyrinopathies | | | |
| Familiar cold autoinflammatory syndrome (FCAS) | CIAS/NALP3 1q44 | Cryopyrin | FCAS: rash, fever and arthralgia after cold exposure |
| Muckle-Wells syndrome (MWS) | | | MWS: recurrent or subchronic urticaria-like lesions, senorineural hearing loss, amyloidosis |
| Chronic infantile neurological cutaneous and articular syndrome (CINCA) | | | CINCA: as above plus mental retardation, chronic aseptic meningitis and bone deformities. All: Good response to IL1 blockade. |
| Granulomatous disorders | | | |
| Blau's syndrome | CARD15/NOD2 16q12 | CARD15 | Early onset (<5 years). Polyarticular granulomatous arthritis, uveitis, skin rash. Good response to anti-TNF monoclonal antibodies. |
| Pyogenic disorders | | | |
| Pyogenic sterile arthritis, pyoderma gangrenosum and acne (PAPA) syndrome | PSTPIP1 15q24-q25.1 | PSTPIP1 | Pyogenic sterile arthritis, pyogenic gangrenosum, cystic acne. Good response to IL1 blockade. |
| Majeed's syndrome | LPIN2 18p | LPIN2 | |
| CRMO (murine) | PSTPIP2 18p | PSTPIP2 | Multifocal osteomyelitis, congenital dyserythropoietic anaemia, inflammatory dermatosis |

Reference:
Euler Compendium on Rheumatic Diseases, Chapter: The autoinflammatory diseases. Marco Gattorno, Katia Stankovic, Maria Antonietta Pelagatti, Gilles Grateau. 375-378.

In alternative embodiments, the methods and kits of the invention can be used to identify those individuals who are at greater risk of developing an inflammatory autoimmune disease.

In one aspect of the invention, at least two samples, or at least three samples, or at least four samples, or at least five samples obtained from the same individual at different points of time are tested for the presence or the amount of mtNA (e.g. mtDNA or mtRNA). This may include collecting data over a period of time. Samples from a patient may be taken at regular intervals. The interval may range from about 2 to about 12 months, or from about 4 to about 8 months, or it ranges from about 5 to about 7 months (e.g. about 6 months). This allows the monitoring of the progression of AID over various periods of time.

Kits and Further Aspects of the Invention

In alternative aspects, the invention provides kits having components for use in the methods of the invention. Such kits may comprise PCR components, as set out in the examples below, including PCR primers specific for an mtDNA or mtRNA sequence and for nuclear DNA or nuclear RNA sequence. Such kits may also include written instructions for carrying out the methods of the invention as described therein.

According to a preferred embodiment, the kit comprises a primer pair capable of specifically amplifying mtDNA or mtRNA in a PCR reaction, at least one oligonucleotide capable of specifically hybridizing with mtNA, or an antibody specifically recognizing mtNA, or a carbohydrate ligand specifically recognizing mtNA, or a non-carbohydrate ligand recognizing mtNA, or an enzyme more or less specifically targeting mtNA at one or several sites. Preferably, the kit further comprises a primer pair capable of specifically amplifying nDNA or nRNA in a PCR reaction. Most preferably, the kit comprises at least one primer pair capable of specifically amplifying mtDNA in a PCR reaction, and at least one primer pair capable of specifically amplifying nDNA in a PCR reaction.

Preferably, the kit comprises additional compounds for determining one or more markers other than AID. That is, the kit may comprise means (e.g., primer pair; oligonucleotide probe; antibody etc.) for determining at least one marker or criterion recited in the above classification criteria 1-19 described above.

Another aspect of the present invention is the use of a primer pair for the diagnosis or diagnostic exclusion of an AID. The primer pair is capable of specifically amplifying a mitochondrial DNA or RNA. Usually suitable oligonucleotide primers have a length of at least 10 nucleotides, preferably of at least 15 nucleotides, more preferably of at least 20 nucleotides. The oligonucleotide primers may be about 15 to 35 nucleotides in length.

Another aspect of the invention is the use of mitochondrial nucleic acids (e.g., mtDNA or mtRNA) as a positive or negative marker for the presence and/or progression and/or activity of an AID such as AAV, large or medium sized vessel inflammation, connective tissue diseases (SLE, systemic sclerosis, polymyositis, dermatomyositis, overlap syndromes and Sjögren's syndrome) inflammatory bowel disease, arthritis, gout, pseudogout, sarcoidosis, Behcet's disease, adult onset Still's disease, Familial Mediterranean Fever, autoinflammatory periodic fever syndromes (e.g. the cryopyrin associated fever syndromes, and others), or ARDS. A preferred embodiment of this aspect corresponds to the preferred embodiments of the method and the use described above. According to a preferred aspect of the invention, mtDNA is used as a marker for the progression of AID.

The invention further concerns a screening method for identifying compounds effective in the treatment of AID, comprising
(a) contacting a test compound with a cell; and
(b) determining the amount of mtNA (e.g. mtDNA or mtRNA) released by the cell. Suitable cells that may be used in the screening method of the invention include, but are not limited to neutrophilic and eosinophilic leucocytes, dendritic cells, Langerhans cells, lymphocytes, natural killer (NK)-cells, macrophages, fibroblasts, endothelial cells, alveolar cells, mucosal cells, platelets, epithelial cells, tubular epithelial cells.

The screening method may further comprise the step of selecting the test compound, if the test compound inhibits the release by the cell of mtNA.

A test compound may be regarded as inhibiting the release by the cell of the mtNA if the release by the cell of the mtNA in the presence of the test compound is reduced by at least 10%, preferably by at least 20%, more preferably by at least 30%, even more preferably by at least 40%, still more preferably by at least 50%, relative to the release by the cell of the mtNA in the absence of the test compound.

The embodiments described herein with respect to AID can be applied to other autoimmune disorders or other inflammatory autoimmune disorders. The embodiments described herein with respect to mtDNA can be applied to other mitochondrial nucleic acids, such as mtRNA.

The preferred embodiments of one aspect of the invention apply to the other aspects of the invention mutatis mutandis.

EXAMPLES

Brief Description of the Tables and Drawings

Table 1. Univariate and multivariate predictors of circulating mtDNA copies/ml plasma in patients with AAV. The linear regression coefficient 'b' represents the amount by which mtDNA increases on average, if the covariate increases by one unit. AAV, ANCA-associated vasculitis; WG, Wegener's granulomatosis; BVAS, Birmingham Vasculitis Activity Score (vs. 3); CRP, C-reactive protein; MPO, myeloperoxidase.

Table 2. Uni- and multivariate predictors of BVAS in patients with AAV. The linear regression coefficient 'b' represents the amount by which BVAS increases on average, if the covariate increases by one unit. For other abbreviations refer to Table 1.

Table 3. Univariate and multivariate predictors of circulating mtDNA copies/ml plasma in patients with SLE. The linear regression coefficient 'b' represents the amount by which mtDNA increases on average, if the covariate increases by one unit. (SLE; Systemic Lupus Erythematosus; SLEDAI, SLE Disease Activity Index, C3 and C4; serum complement components 3 and 4, C3d; cleavage product of serum complement component C3)

Table 4. Uni- and multivariate predictors of SLEDAI among patients with SLE. The linear regression coefficient 'b' represents the amount by which the SLEDAI increases on average, if the covariate increases by one unit. For other abbreviations refer to Table 3.

FIG. 1. Anti-PR3 autoantibody serum levels in studied patients with AAV and non-AID control subjects. The PR3-ELISA has a cut-off value of 10 U/L. The bars within each group represent median values.

Figure 2:
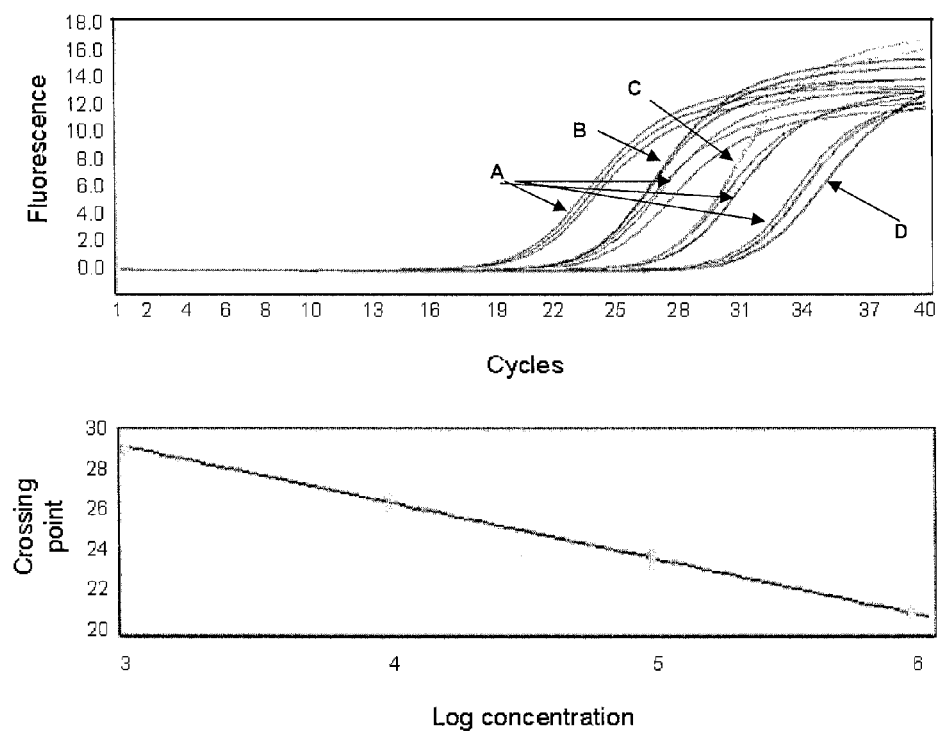

FIG. 2 The upper panel plots LightCycler PCR amplifications curves of mtDNA (B), nDNA (C) and 10-fold dilutions of standard plasmid (A), each in triplicates. The negative control ($H_2O$) is labeled with D. The lower panel shows a representative standard curve obtained from serial plasmid dilutions in triplicates (gray dots) which demonstrates a PCR efficiency of 1.939 per cycle (with an efficiency of 2 being the theoretical optimum). The crossing point was automatically calculated by the LightCycler software.

Figure 3A:
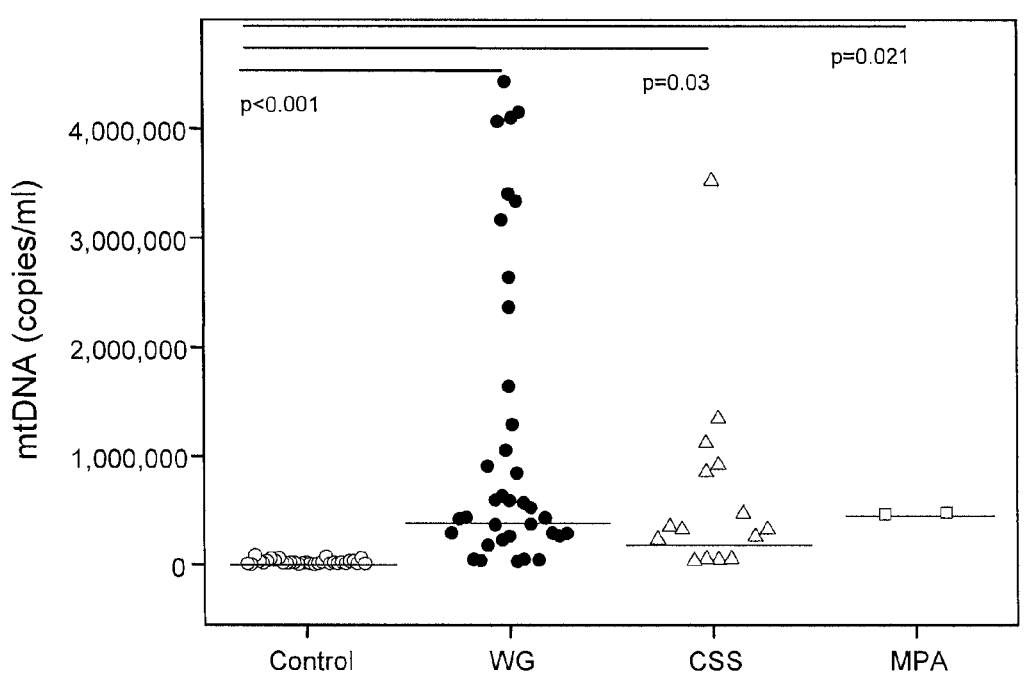

FIG. 3. Correlations between BVAS and its independent predictors which were identified by multivariate analysis (neutrophil numbers and mtDNA copies) in patients with AAV. For comparison the correlation between BVAS and CRP is also plotted. For correlation coefficients see Table 2.

Figure 4:
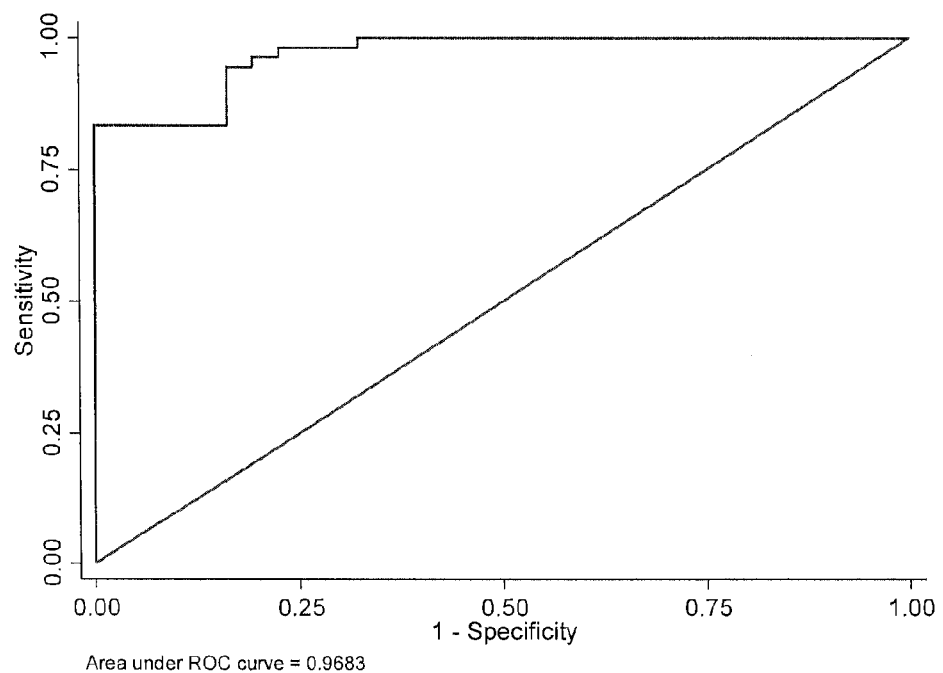

FIG. 4. Receiver operating characteristic (ROC) curve for mtDNA testing in all AAV patients (irrespective of vasculitis activity).

Figure 5:
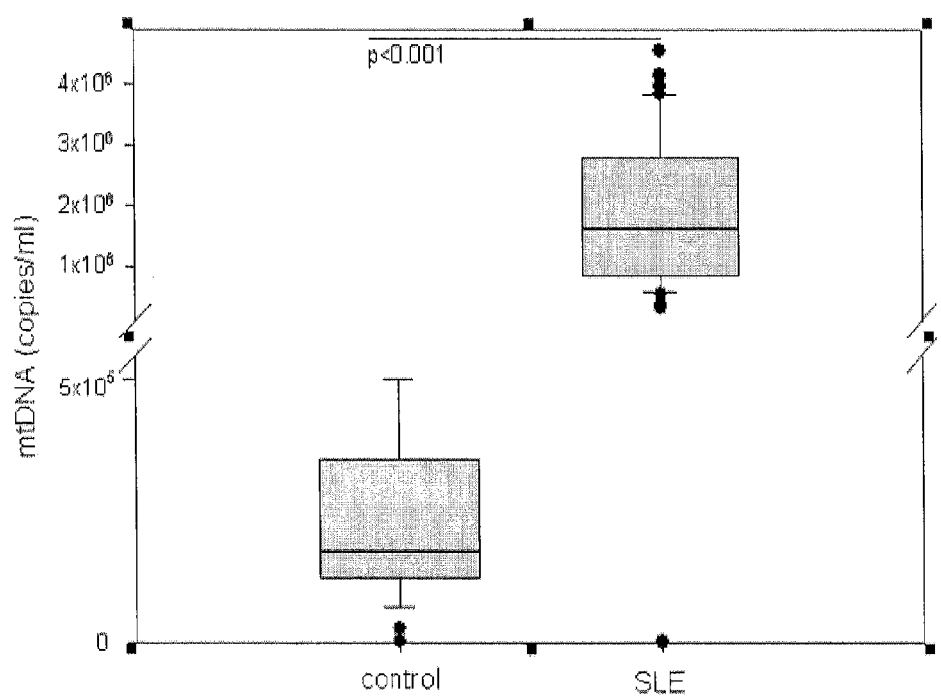

FIG. 5. Compared to plasma from control subjects (n=26) the mtDNA amount in the plasma of individuals diagnosed with SLE (n=41) is significantly increased (p<0.001). The highest measured mtDNA amount of control subjects is lower than the lowest mtDNA amount in the SLE subjects. The 'whiskers' in the plot represent 5% and 95% percentiles.

Figure 6A:
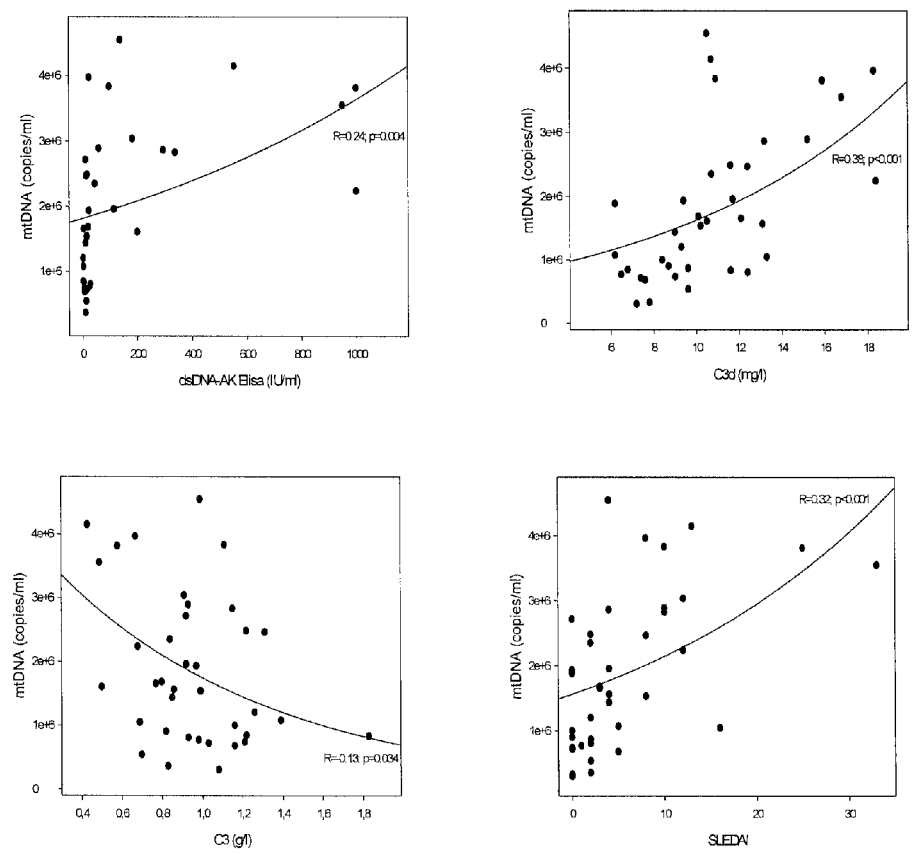

FIG. 6A. Statistically significant univariate correlations between circulating mtDNA levels in plasma and potential other SLE disease activity indicators. Among all SLE patients, the amount of mtDNA correlated positively with the dsDNA-antibody ELISA test result (R=0.24; p=0.004), the amount of the complement factor 3 split product C3d in the subjects plasma (R=0.38; p<0.001; B) and the SLE disease activity in terms of SLEDAI (R=0.32; p<0.001). The mtDNA was inversely correlated with the amounts of native component factor 3 (C3) in subjects plasma (R=−0.13; p<0.001).

Figure 6B:
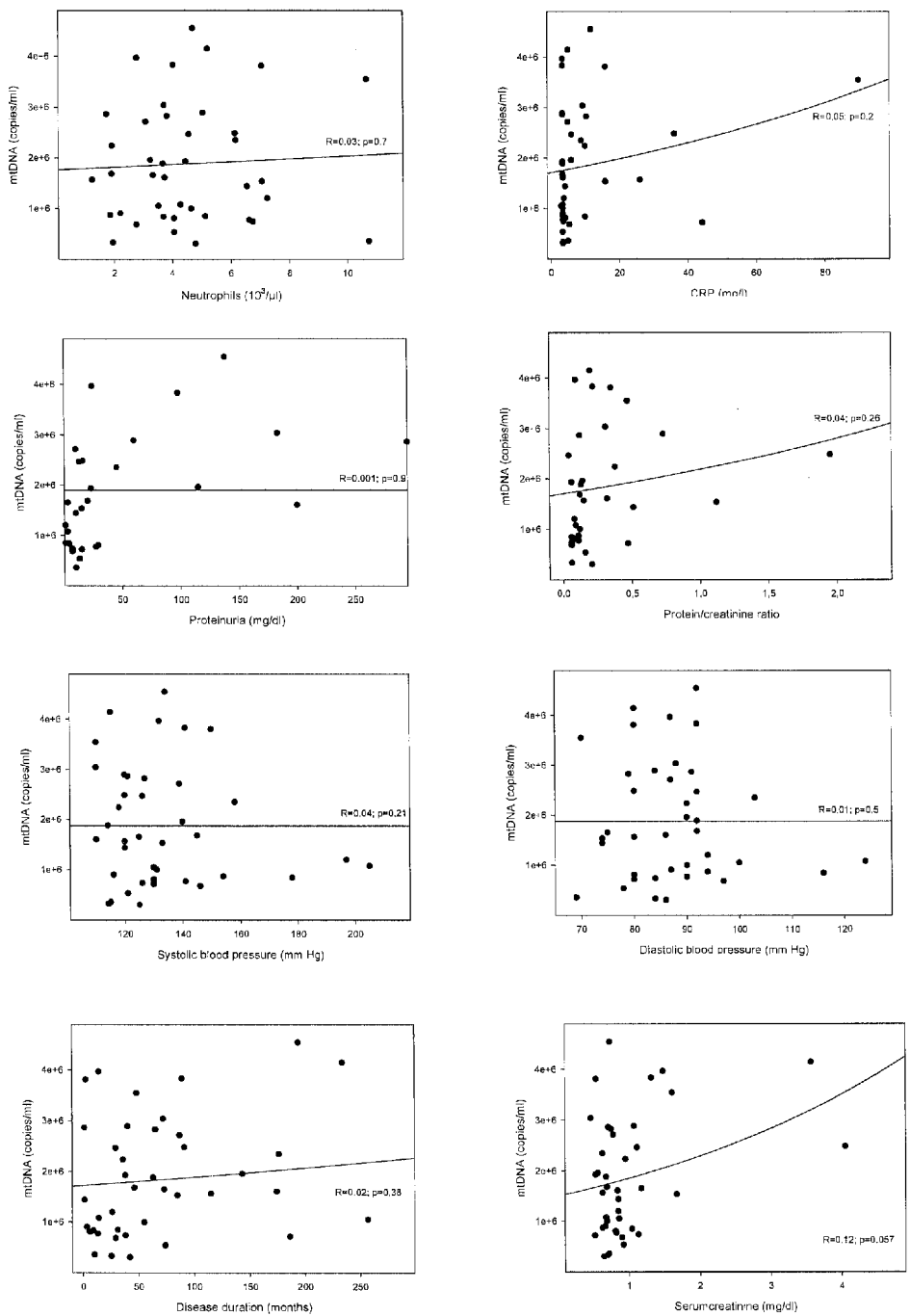

FIG. 6B. Circulating mtDNA plasma amounts did not correlate with peripheral blood neutrophil numbers the C-reactive protein (CRP), arterial hypertension, disease duration and serum creatinine.

Figure 7:
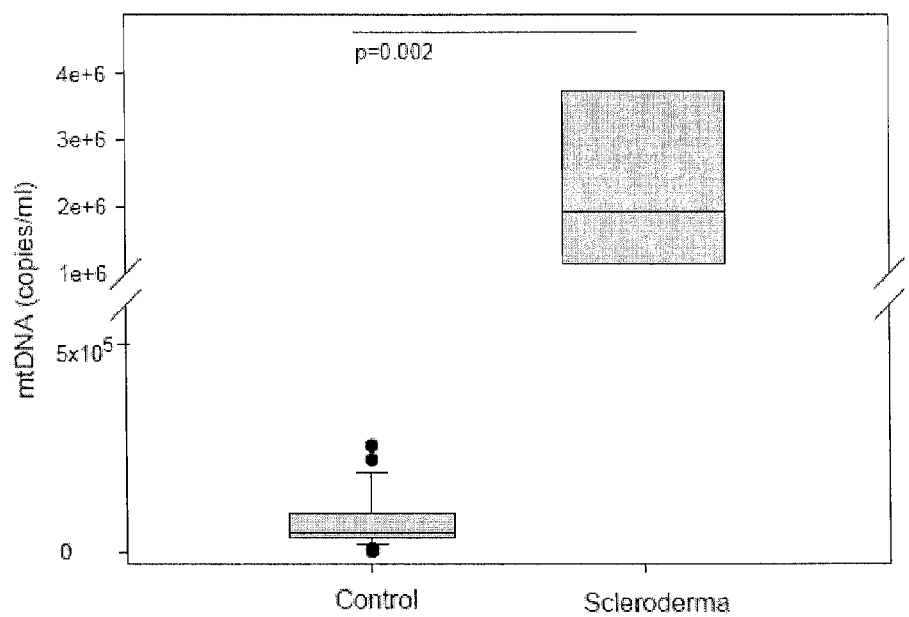

FIG. 7. Box Blot comparison between control subjects (n=26) and subjects with scleroderma (SSc, systemic sclerosis, n=4). The mtDNA amount was significantly higher in the scleroderma group than in control subjects (p=0.002). The bars within each group represent median values, the 'whiskers' in the plot represent 5% and 95% percentiles.

Figure 8:
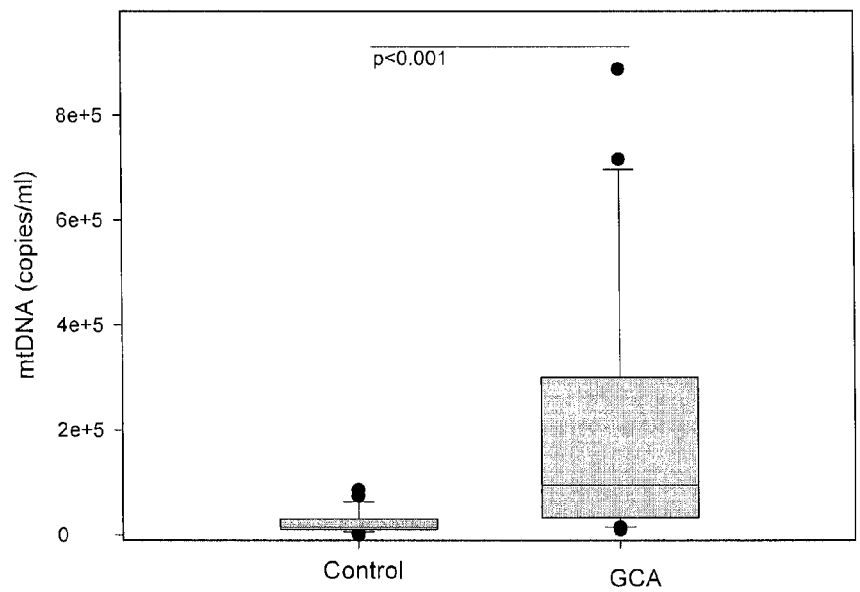

FIG. 8. Compared to plasma from control subjects (n=26) the mtDNA amount in the plasma of individuals with giant cell arteriitis (GCA) (n=25) was significantly increased (p<0.001). The bars within each group represent median values, the 'whiskers' in the plot represent 5% and 95% percentiles.

Figure 9:
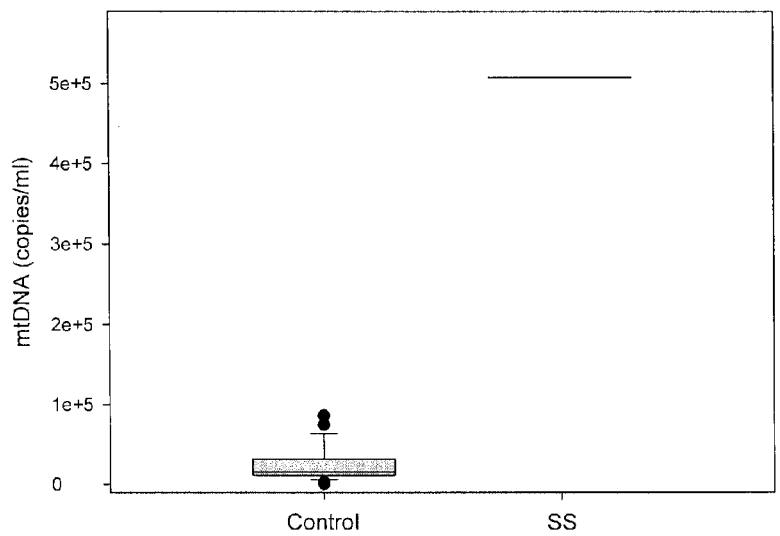

FIG. 9. Circulating mtDNA copy numbers in the plasma of control subjects (n=26) compared to Sjögren's syndrome (SS, n=1). The bars within each group represent median values, the 'whiskers' in the plot represent 5% and 95% percentiles.

Figure 10:
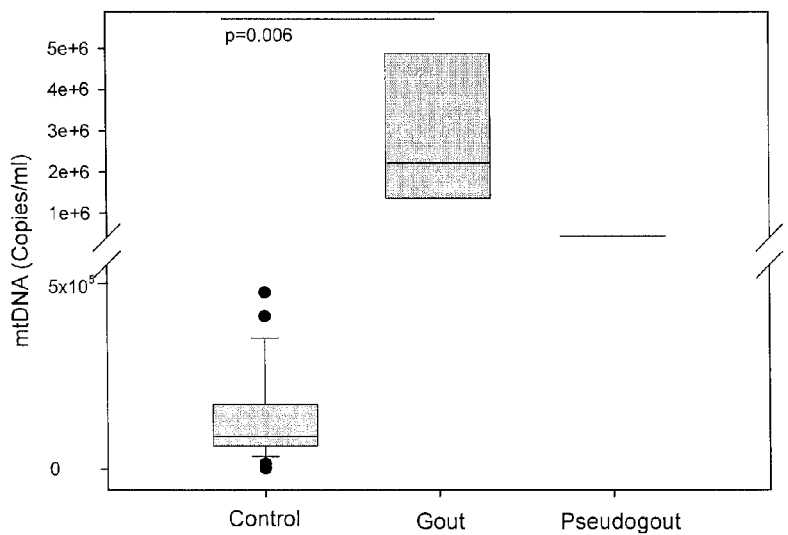

FIG. 10. Free circulating mtDNA plasma amounts in crystal arthopathies such as active gout (n=3) and active pseudogout (n=1). The bars within each group represent median values, the 'whiskers' in the plot represent 5% and 95% percentiles.

EXAMPLE 1

ANCA-Associated Vasculitis (AAV)

Methods

Patients with AAV and Controls

After ethics committee approval, subjects willing to provide signed written consent were consecutively recruited from July 2010 until March 2011. This study included adult patients attending the Freiburg and Basel Departments of Rheumatology that were classified as AAV (WG, CSS or MPA)[15]. Exclusion criteria consisted of active bacterial or viral infections, trauma, malignancy, recent surgery, as well as concomitant other systemic AID (e.g. rheumatoid arthritis or inflammatory bowel disease)[16,17].

Healthy adult volunteers and subjects hospitalized for osteoporotic spine fractures or herniated intervertebral disks without concomitant inflammatory disease, as also evidenced by a normal C-reactive protein (CRP), served as controls.

In all subjects 9 ml of venous peripheral blood was collected in an EDTA tube (Sarstedt, Nümbrecht, Germany). Immediately after blood withdrawal, the EDTA-blood was centrifuged (Hettich, Rotanta 460, Germany) at 2000×g for 5 min at room temperature. The plasma was carefully collected without disturbing or aspirating the buffy coat, aliquoted and placed in a −80° C. freezer until processing. In parallel, a serum sample was taken for the centralized quantification of CRP, anti-PR3 and anti-MPO autoantibody levels (Orgentec, Mainz, Germany). As part of their routine care, nasal carriage of *S. aureus* was assessed with a swab culture. Patients' arterial blood pressure was measured to detect arterial hypertension, defined as systolic pressure above 140, or diastolic pressure above 90 mmHg. Vasculitis activity was scored by means of the Birmingham Vasculitis Activity Score (BVAS, version 3)[18], a score which has been shown to correlate with treatment decision[19].

Quantification of Circulating DNA Copy Numbers

Total DNA was extracted from plasma (1 ml) with the QIAamp DNA isolation kit (Qiagen, Hilden, Germany). MtDNA and nuclear DNA (nDNA) copy numbers were quantified in a Roche LightCycler 480 real time polymerase chain reaction (PCR) system, equipped with the Light Cycler 480 multiwell plate 384 (Roche Diagnostics GmbH, Mannheim, Germany) by means of a DNA intercalating dye (SYBR Green I)[20]. The mtDNA ATP-6 gene was amplified between nucleotide positions 8981 and 9061 with the forward primer 5'-ACCAATAGCCCTGGCCGTAC-3' (SEQ ID NO:1) and the backward primer 5'-GGTGGCGCTTC-CAATTAGGT-3' (SEQ ID NO:2). For the detection of nDNA we selected exon number 8 of the glyceraldehyde 3-phosphate dehydrogenase (GAPDH) gene between nucleotide positions 4280 and 4342 and used the forward primer 5'-CGGGGCTCTCCAGAACATC-3' (SEQ ID NO:3) and the backward primer 5'ATGACCTTGCCCACA-GCCT-3' (SEQ ID NO:4). Each 25 µl PCR reaction contained 20 ng of genomic DNA, 100 nM probe, 200 nM primers and LightCycler 480 SYBR Green I Master Mix (Roche Diagnostics GmbH, Mannheim, Germany). The PCR reaction consisted of an initial DNA denaturation step of 5 min at 95° C., followed by 45 cycles of 15 seconds at 95° C., alternating with 1 min at 60° C. and 15 seconds at 72° C. The specificity of the amplified PCR product was assessed with a melting curve. Absolute mtDNA and nDNA copy numbers were calculated using serial dilutions of plasmids with known copy numbers[20]. Amplifications of mitochondrial and nuclear products were performed in triplicates. A negative control and a standard curve were included in each run.

Statistical Analysis

Between groups results were compared by unpaired t-test or Wilcoxon-analysis, as appropriate. Within groups, variables were tested by means of univariate and multivariate linear regression analysis. Data analysis was performed using STATA 11.0 (stataCorp Inc., College Station, Tex., USA). Regressions were plotted with Sigma Plot version 8.0 (SPSS Inc., USA). All statistical tests were two-tailed and a p-value<0.05 was considered statistical significant.

Results

Participants

Thirty one healthy controls (18 females) volunteered for this study. Their mean age was 43 years (range 20-75 years). In all control patients, the CRP was within normal limits and ANCA were negative.

Fifty four patients (19 females) with AAV fulfilled were included. Their mean age was 58 years (range 26-81 years) and their mean disease duration 5.4 years (range 0.1-23.5 years).

40 patients had WG, twelve had CSS and two had MPA. 22 AAV patients had a history of renal and 37 patients had a history of pulmonary involvement. Among the patients with WG 6 had localized WG, and 34 had systemic WG. The median BVAS of all AAV patients at the time of blood collection was 5 (interquartile range (IQR) 1-7) and the median prednisone equivalent was 8 mg/day (IQR 5-15).

At the time of mtDNA-analysis, 59% of the AAV patients had an elevated PR3-ANCA based on ELISA (>10 U/mL). The median serum PR3-level of all AAV-patients was 49 U/L (IQR 1-142, FIG. 1). 8% of the AAV patients had an elevated MPO-ANCA based on ELISA (>20 U/mL), 2 of these patients had WG, one had CSS, and one patient had MPA. The median CRP of the AAV patients was 1.7 mg/L (IQR 1.7-8.0), and the median neutrophil count was $6.0*10^9$/mL (IQR 5.3-8.0). The serum creatinine was elevated (>1.2 mg/L) in 13 subjects with AAV. The nasal swab was positive for *S. aureus* in nine of 34 tested AAV patients, eight of which had WG.

Assay Quality

Our assay was highly accurate and reproducible (FIG. 2). Among all AAV-plasma samples the intra-run coefficient of variation (standard variation of the triplicates in one run divided by the mean) was 2.8% for the mtDNA and 5.3% for nDNA amplicon. The inter-run coefficient of variation (the standard variation in two different runs divided by the mean) was 5.4% for both mtDNA and nDNA.

We also investigated the impact of hemolysis by repeatedly forcing blood rapidly through a thin (21 G) needle. This procedure caused a visible red tinge in the plasma but increased the detected mtDNA amounts by only 5% compared with non-hemolytic aliquots.

Circulating Mitochondrial DNA Copy Numbers

The median mtDNA copy number in control plasma was 15,400/ml (IQR 10,992-31,233). The highest mtDNA copy number among all 31 examined control plasma samples was 86,333/ml and the lowest measurement was 368/ml.

In all AAV patients, the median number of circulating mtDNA copies was 449,683/ml (IQR 257,500-1,120,000). Compared with the median mtDNA copies in healthy volunteers, this represents an increase by a factor of 29.2 (p<0.001). The lowest mtDNA copy number in AAV patients was 27,167/ml and the highest was 4,426,666/ml. The median mtDNA copy number in the 12 patients with CSS was 323,667/ml (IQR 47,750-498,717) and 473,017/ml in the 2 patients with MPA.

Nine of the 54 AAV patients (16.7%) had circulating mtDNA copies below the highest value (86,333/ml) of the 31 healthy controls. Four of these nine AAV patients had CSS and 5 had WG. The mtDNA plasma levels of WG, CSS and MPA subgroups are plotted in FIG. 3A.

Predictors of mtDNA Copies

Similar to the situation in healthy volunteers, mtDNA copy numbers in AAV patients were not correlated with gender or age on univariate analysis (Table 1). Circulating mtDNA levels were also not associated with the presence or absence of pulmonary or renal involvement in the patient's history. Similarly, mtDNA plasma levels were also not associated with arterial blood pressure, circulating anti-PR3 autoantibody or anti-MPO autoantibody levels, serum creatinine, or *S. aureus* nasal carriage at the time of blood collection (Table 1). Corticosteroid medication did not suppress circulating mtDNA-levels. In fact, mtDNA copies correlated with the daily consumption of prednisone equivalents, probably as a result of disease activity (see below). On univariate analysis of all AAV patients, circulating mtDNA plasma levels were also correlated with peripheral blood neutrophil counts ($R^2=0.138$, p=0.006) and serum CRP ($R^2=0.339$, p<0.001) but the correlation coefficient was highest with BVAS ($R^2=0.588$, p<0.001). In the WG subgroup the covariates that were significant on univariate comparison were neutrophil count, ($R^2=0.175$) serum CRP ($R^2=0.368$), and BVAS ($R^2=0.605$, Table 1). After multivariate analysis, only BVAS and CRP remained predictive for circulating mtDNA-levels. The adjusted $R^2$ values in the multivariate models were 0.678 for the AAV patients and 0.693 for the WG subgroup, indicating that CRP contributes only little to the goodness of fit in both models and that BVAS is the major driving factor and best predictor of mtDNA plasma levels.

TABLE 1

|  | All AAV (n = 54) | | WG only (n = 40) | |
| --- | --- | --- | --- | --- |
|  | b (95% CI) | p | b (95% CI) | p |
| Univariate analysis | | | | |
| Gender |  | 0.40 |  | 0.37 |
| Patient age (years) |  | 0.11 |  | 0.47 |
| Disease duration (years) |  | 0.86 |  | 0.66 |
| BVAS vs.3 | 170656 (130489, 210823) | <0.001 | 173088 (126542, 219633) | <0.001 |
| Arterial hypertension |  | 0.43 |  | 0.49 |
| Blood neutrophil count ($10^9$/L) | 185623 (55290, 315956) | 0.006 | 215465 (59362, 371568) | 0.008 |
| Serum anti-PR3 antibody (U/L) |  | 0.68 |  | 0.91 |
| Serum anti-MPO antibody (U/L) |  | 0.48 |  | 0.43 |
| Serum CRP (mg/L) | 60539 (36781, 84298) | <0.001 | 60173 (34271, 86074) | <0.001 |
| Serum creatinine (mg/L) |  | 0.99 |  | 0.71 |
| *S. aureus* nasal carriage |  | 0.83 |  | 0.90 |
| Multivariate analysis | | | | |
| BVAS vs. 3 | 149112 (105570, 192653) | <0.001 | 150749 (98625, 202874) | <0.001* |
| Serum CRP (mg/L) | 35349 (15169, 55530) | 0.001 | 34466 (11202, 57729) | 0.005 |
| Blood neutrophil count ($10^9$/L) |  | 0.37 |  | 0.41 |

Circulating Nuclear DNA Copy Numbers

We also analyzed circulating nDNA copy numbers in order to exclude the possibility of impaired DNAse activity as a mechanism for the observed enhancement of mtDNA levels. If DNAse activity was indeed nonspecifically impaired in AAV, we would expect also an enhancement of nDNA levels. The median nDNA copy number in control plasma was 5,747/ml (IQR 2,863-9,798) but this value did not differ from AAV patients (median nDNA copy number 5,125/ml, IQR 2,222-11,233, p=0.93). In both, AAV and WG patients, nDNA levels were neither associated with age or gender, nor were they correlated univariately, or multivariately with any of the variables in Table 1. This finding does not support a nonspecific impairment of DNases as the mechanism for the observed mtDNA increase in AAV.

We then calculated the ratio of circulating mtDNA and nDNA copy numbers in each plasma sample. The median mtDNA/nDNA ratio was 3.2 (IQR 1.9-8.5) in control patients, and 246 (IQR 38-562) in AAV patients. This finding supports the hypothesis of an enhanced release of mtDNA. The mtDNA/nDNA ratio did neither univariately, nor multivariately correlate with any of the patients' characteristics listed in Table 1, including CRP and neutrophil peripheral blood counts.

Predictors of BVAS

Figure 3B:
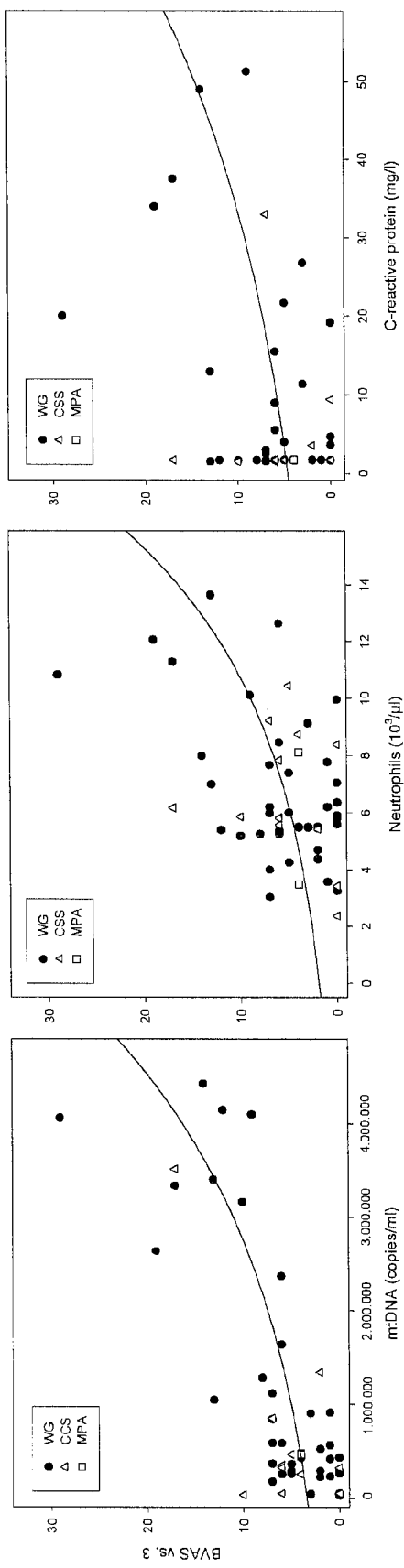

We next analyzed by means of linear regression analysis, if mtDNA plasma levels could be useful to predict disease activity in terms of BVAS in AAV (Table 2). On univariate comparisons, significant variables were blood neutrophil count ($R^2=0.207$), CRP levels ($R^2=0.184$), and mtDNA ($R^2=0.588$). These factors were also significant in the isolated analysis of the subgroup of WG patients, with an $R^2$ of 0.252 for blood neutrophil count, 0.220 for CRP levels, and the highest $R^2$ (0.605) for mtDNA (FIG. 3B). On multivariate analysis, only mtDNA-levels and neutrophil counts remained covariates in the model, generating an adjusted $R^2$ value of 0.635 in AAV, and 0.657 in WG. As may be expected from the findings above, nDNA-copy numbers, and mtDNA/nDNA-ratio did not correlate with BVAS. Taken together, our results indicate, that among all variables listed in Table 2, mtDNA plasma levels are the best predictor of disease activity in AAV.

components[21]. Although PR3 antibodies prime neutrophils for NETosis in vitro, we were surprisingly unable to detect a direct relationship between mtDNA and PR3 levels in our clinical study. The lack of a correlation between PR3-ANCA and mtDNA plasma levels suggests the in vivo presence of either counterinflammatory mechanisms, additional proinflammatory stimuli, or non neutrophil sources of mtDNA liberation[7] which obscure a measurable relationship between ANCA and mtDNA plasma levels, while still allowing for a good correlation between mtDNA and vasculitis activity.

Interestingly, the transfer of PR3-ANCA-containing IgG into wild-type mice did not induce systemic vasculitis[4,22], whereas clinically relevant concentrations of mtDNA do not only activate neutrophils via TLR9, but do induce both local

TABLE 2

|  | All AAV (n = 54) | | WG only (n = 40) | |
|---|---|---|---|---|
|  | b (95% CI) | p | b (95% CI) | p |
| Univariate analysis | | | | |
| Gender |  | 0.41 |  | 0.62 |
| Patient age (years) |  | 0.94 |  | 0.70 |
| Disease duration (years) |  | 0.28 |  | 0.31 |
| Arterial hypertension |  | 0.84 |  | 0.79 |
| Blood neutrophil count | 1.03 (0.46, 1.60) | 0.001 | 1.18 (0.49, 1.86) | 0.001 |
| Serum anti-PR3 antibody (U/L) |  | 0.56 |  | 0.71 |
| Serum anti-MPO antibody (U/L) |  | 0.79 |  | 0.97 |
| Serum CRP (mg/L) | 0.20 (0.08, 0.32) | 0.002 | 0.21 (0.08, 0.34) | 0.003 |
| Serum creatinine (mg/L) |  | 0.89 |  | 0.77 |
| S. aureus nasal carriage |  | 0.96 |  | 0.84 |
| mtDNA (copies/ml plasma) | 0.008 (0.006, 0.011) | <0.001 | 0.008 (0.006, 0.011) | <0.001 |
| nDNA (copies/ml plasma) |  | 0.76 |  | 0.72 |
| mtDNA/nDNA-ratio |  | 0.13 |  | 0.23 |
| Multivariate analysis | | | | |
| Serum CRP (mg/L) |  | 0.30 |  | 0.37 |
| Blood neutrophil count ($10^9$/L) | 0.53 (0.07, 0.99) | 0.03 | 0.59 (0.03, 1.16) | 0.04 |
| mtDNA (copies/ml plasma) | 0.008 (0.006, 0.011) | <0.001 | 0.008 (0.005, 0.011) | <0.001 |

Diagnostic Utility of Circulating mtDNA

We examined the diagnostic utility of circulating mtDNA plasma level testing, if it was applied as for the diagnosis of AAV to our study population (all healthy volunteers plus all patients with AAV). The receiver operating characteristic (ROC) curve determined an optimal cut-off value of 178,000 mtDNA copies/ml plasma with an area under the ROC curve of 0.968 (FIG. 4), producing a test sensitivity of 83.3%, a specificity of 100%, and a positive likelihood ratio of about 25.8. In the WG subgroup, the area under the ROC curve would be 0.975 and the same cut-off would result in a sensitivity of 87.5%, a specificity of 100%, and a positive likelihood ratio of about 27.1.

In the 9 AAV patients with circulating mtDNA copies below the highest value of controls, the BVAS was 0 in six patients; and 3, 6 and 10 in the three remaining AAV patients, respectively. This observation indicates that the positive predictive value of mtDNA-analysis would be further enhanced, if only active vasculitis, rather than a mix of AAV patients with both, active and inactive disease were considered.

Discussion

Our results document a profound upregulation of circulating mtDNA copy numbers in the plasma of patients with AAV, strengthening the evidence for an involvement of innate immunity in the pathogenesis of this form of vasculitis.

It has been demonstrated previously that the in vitro stimulation of primary human leukocytes with anti-PR3 antibodies enhances their TLR9 expression and promotes their release of cytokines upon stimulation with microbial and distant organ inflammation[4,23]. Although components of S. aureus are also known to prime neutrophils for NETosis in vitro[13,24], we failed to detect a relationship between S. aureus nasal colonization and mtDNA content.

Our results suggest that the pathogenetic relevance of circulating mtDNA may exceed that of PR3-ANCA[4]. Another hypothesis to be explored is that PR3-ANCA and S. aureus participate in triggering neutrophil activation locally, whereas systemic organ involvement depends on mtDNA. The role of neutrophils as a possible source of mtDNA is indicated by the observation that AAV is prevented by the depletion of neutrophils in mouse models[25] and our observation that neutrophil numbers are univariately associated with circulating mtDNA levels. We however cannot exclude the possibility that platelets which are activated in WG and which contain mtDNA but not nDNA represent another source of circulating mtDNA[26].

We failed to detect an increase of circulating nDNA in AAV. The unaltered nDNA plasma levels in AAV argue against an unspecific impairment of DNA-degradation as a possible mechanism of our findings and either point towards disparate degradation of circulating DNA species, or an isolated enhancement of mtDNA release. It has been suggested previously that the NETs released from eosinophils consist of mtDNA[6,7], but such link has not been made for NETs released from neutrophils[13]. It has even been suggested that NETs formed in response to S. aureus predominantly contain nDNA[24]. The unaltered nDNA copy numbers in our study, and the observation that nDNA is not inflammatogenic in vivo[23], also suggest that the quantification of nDNA copy numbers does not enhance the performance of a possible diagnostic test.

Our study demonstrates that elevated circulating mtDNA copy numbers detect active AAV with good sensitivity. Even more importantly, circulating mtDNA copy numbers were associated with vasculitis activity in our selected population, whereas possible other indicators of disease activity such as CRP and PR3 levels either had a weaker or no correlation with BVAS, consistent with previous observations[19,27,28].

EXAMPLE 2

Systemic Lupus Erythematosus

Systemic lupus erythematosus (SLE) is an AID characterized by B-cell activation and autoantibody production against a variety of autoantigens. Another key characteristic of SLE consists of the presence of chronically activated plasmacytoid dendritic cells, which secrete type I interferons, such as IFN-alpha. Autoantibodies are also formed against cellular blood components and lead to anemia, thrombopenia, lymphopenia and neutropenia. Viral infections trigger immune responses via recognition of viral DNA through TLR9 in endosomes[29]. Characteristically, SLE disease flares are associated with a rise in circulating autoantibodies against double stranded DNA (anti-dsDNA autoantibodies). It has recently been demonstrated that sera of SLE patients contain antibody and non-antibody inhibitors which impair NET-degradation by DNAse in vitro[30] and that the lack of extracellular DNAse is associated with a SLE phenotype[31,32]. The formation of NETs in SLE patients themselves or the nature and quantity of circulating DNA (mtDNA or nDNA) levels in body compartments has however not been investigated in humans. It has been demonstrated in mice, that pharmacological inhibition of TLR9, the receptor for circulating mtDNA also blocks autoantibody production in human B cells from SLE patients[33]. CpG-induced TLR9 stimulation caused autoantibody secretion in patients with active disease and in the majority of patients in clinical remission[33]. Inhibition of MyD88 completely blocked the de novo generation of plasma cells and the secretion of autoantibodies[33].

Thus, TLR9-dependent activation of memory B cells by pathogens could be one of the mechanisms triggering relapses in SLE[33]. Indeed, in a model of SLE skin inflammation, NETS were formed in a TLR9 dependent fashion[34]. Neutrophils derived from SLE patients undergo accelerated cell death by NETosis in culture, with NETs being potent activators of plasmacytoid dendritic cells[35].

We analyzed circulating mtDNA plasma levels in 40 patients with SLE (mean age 45.6 years). In SLE patients, mtDNA copy numbers, but not nDNA copy numbers were significantly increased compared to plasma samples from control individuals (n=26, p<0.001). The mean mtDNA copy number in SLE patients was 1,858317, the minimal copy number was 303,000 and the maximal copy number was 4,543,333. Thus, the mtDNA copies in SLE were even higher than those in AAV. Regardless of SLE activity, the lowest test result among all SLE-patients was higher than the highest value among all control samples, indicating that low mtDNA test results can be used to exclude the diagnosis of SLE. Conversely, in the population examined, mtDNA testing has a 100% diagnostic specificity for this AID.

Within the group of SLE patients, circulating mtDNA copies/ml plasma were predicted by a high score of the Systemic Lupus Erythematosus Disease Activity Index (SLEDAI), low levels of complement component C3, high levels of the complement split product C3d and high levels of circulating anti-dsDNA antibodies in the patients serum on univariate analysis (Table 3). On multivariate analysis, SLEDAI, C3d and CRP remained significant, indicating that mtDNA levels are a function of disease activity in SLE (Table 3).

When we reversed the question and asked what best predicted disease activity in SLE, as measured by the SLEDAI. We found that mtDNA levels were highly predictive of disease activity on univariate and multivariate analysis (Table 4).

TABLE 3

Predictors of cell free plasma mtDNA levels in SLE

| | SLE (n = 40) | |
|---|---|---|
| | b (95% CI) | p |
| Univariate analysis | | |
| Gender | | 0.692 |
| Patient age (years) | | 0.788 |
| Disease duration (years) | | 0.359 |
| SLEDAI | 95555 (48430, 142680) | <0.001 |
| C3 (g/l) | −1662563 (−3094998, −230128) | 0.024 |
| C4 (g/l) | | 0.471 |
| C3d (mg/l) | 205004 (113005, 297002) | <0.001 |
| Anti-dsDNA antibody levels (IU/ml) | 2045 (713, 3377) | 0.004 |
| Blood neutrophil count (10$^9$/L) | | 0.635 |
| Serum creatinine (mg/dl) | 559193(40317, 1078069) | 0.035 |
| Serum CRP (mg/L) | | 0.137 |
| Proteinuria (mg/dl) | | 0.271 |
| Multivariate analysis | | |
| SLEDAI | 93386 (40306, 146465) | 0.002 |
| C3d (mg/l) | 136461 (40190, 232733) | 0.008 |
| Serum CRP (mg/L) | −18463 (−36498, −428) | 0.045 |

TABLE 4

Predictors of SLEDAI

| | SLE (n = 40) | |
|---|---|---|
| | b (95% CI) | p |
| Univariate analysis | | |
| Gender | | 0.585 |
| Patient age (years) | | 0.177 |
| Disease duration (years) | | 0.846 |
| C3 (g/l) | −16.49 (−26.32, −6.66) | 0.002* |
| C4 (g/l) | | 0.195 |
| C3d (mg/l) | 1.34 (0.79, 1.88) | <0.001* |
| Anti dsDNA ELISA (IU/ml) | 0.02 (0.01, 0.03) | <0.001* |
| Blood neutrophil count (10$^9$/L) | 1.10 (0.10, 2.10) | 0.031* |
| Serum creatinine (mg/dl) | | 0.223 |
| Serum CRP (mg/L) | 0.23 (0.12, 0.35) | <0.001* |
| Protein/creatinine ratio | | 0.445 |
| mtDNA(copies/ml plasma) | 3.34e$^{-06}$ (1.70e$^{-06}$, 4.99e$^{-06}$) | <0.001* |
| mtDNA/nDNA-Ratio | 0.001 (−0.002, 0.004) | 0.557 |
| Multivariate analysis | | |
| Anti dsDNA ELISA (IU/ml) | 0.01 (0.005, 0.02) | 0.001 |
| mtDNA (copies/ml plasma) | 3.24e$^{-06}$ (1.85e$^{-06}$, 4.64e$^{-06}$) | <0.001 |
| Serum CRP (mg/L) | 0.09 (0.01, 0.17) | 0.029 |
| Neutrophil blood count | 0.85 (0.15, 1.55) | 0.021 |

EXAMPLE 3

Systemic Sclerosis

Systemic sclerosis (SSc, scleroderma) is a severe AID with multiorgan involvement. The pathogenesis of SSc is poorly understood. SSc leads to fibrotic changes in skin and many organs, but already in early disease stages a pronounced microangiopathy can be detected with endothelial cell activation and consecutive apoptosis[36]. Toll like receptor 3 (TLR3) participates in endothelial cell activation and TLR3 stimulation has recently been shown to activate dermal fibrosis[37,38], whereas TLR9 and neutrophilic granulocytes have not been found to have a central role in the pathogenesis of SSc so far[36]. In a small cohort of patients with SSc (n=4), we found substantially elevated levels of circulating mtDNA in the plasma (FIG. 7).

EXAMPLE 4

Giant Cell Arteriitis (GCA)

The giant cell arteriitis and the Takayasu arteriitis are AID which lead to an inflammation of large arteries. The inflammation probably does not originate in the lumen of the vascular bed, but rather in the adventitia[39]. This represents an important difference to AAV. Another difference is, that in GCA, neither neutrophilic neutrophils, nor TLR9 (which recognizes double stranded nucleic acids) are known to play an important role in the pathogenesis[39]. Nevertheless, we found substantially elevated levels of circulating mtDNA in patients with GCA (FIG. 8)

EXAMPLE 5

Plasma samples from patients suffering from AAV, SLE, Rheumatoid arthritis or scleroderma (systemic sclerosis) were analysed for the concentration of circulating mtDNA.

The analysis of mtDNA was carried out as described in Example 1, except for the centrifugation step. In all subjects 9 ml of venous peripheral blood was collected in an EDTA tube. Immediately after blood withdrawal, the EDTA-blood was centrifuged at 7250×g for 10 min at room temperature.

The results are summarized in the following table.

| ID | Disease | Average mtDNA (absolute copies) | Standard deviation | n |
|---|---|---|---|---|
| 1 | Healthy control persons | 2016 | 1958 | 11 |
| 2 | AAV | 228860 | 345044 | 24 |
| 3 | SLE | 214480 | 356479 | 19 |
| 4 | Rheumatoid arthritis | 291943 | 925658 | 24 |
| 5 | Scleroderma | 40977 | 36335 | 5 |

EXAMPLE 6

Other AID

Circulating mtDNA levels were also found to be elevated in the plasma of patients with Sjögren's syndrome (FIG. 9) and inflammatory crystal deposition disease in terms of gout and pseudogout (chondrocalcinosis) (FIG. 10).

Furthermore, elevated levels of circulating mtDNA were found in the plasma of patients suffering from inflammatory bowel disease such as Crohn's disease and colitis ulcerosa, as shown in the following table, wherein the amount of mtDNA is indicated in absolute copy numbers per milliliter plasma.

| Subject ID | Inflammatory bowel disease | Preparation of plasma sample according to | mtDNA copies/ml plasma |
|---|---|---|---|
| 1 | Crohn's disease | Example 1 | 283333 |
| 2 | Crohn's disease | Example 5 | 1025300 |
| 3 | Crohn's disease | Example 5 | 108150 |

REFERENCE LIST

1. Kawai T, Akira S. The role of pattern-recognition receptors in innate immunity: update on Toll-like receptors. *Nat Immunol* 2010; 11:373-384.
2. Santiago-Raber M L, Baudino L, Izui S. Emerging roles of TLR7 and TLR9 in murine SLE. *J Autoimmun* 2009; 33:231-238.
3. Sun S, Rao N L, Venable J, Thurmond R, Karlsson L. TLR7/9 antagonists as therapeutics for immune-mediated inflammatory disorders. *Inflamm Allergy Drug Targets* 2007; 6:223-235.
4. Zhang Q, Raoof M, Chen Y, Sumi Y, Sursal T, Junger W, et al. Circulating mitochondrial DAMPs cause inflammatory responses to injury. *Nature* 2010; 464: 104-107.
5. Brinkmann V, Reichard U, Goosmann C, Fauler B, Uhlemann Y, Weiss D S, et al. Neutrophil extracellular traps kill bacteria. *Science* 2004; 303:1532-1535.
6. Yousefi S, Mihalache C, Kozlowski E, Schmid I, Simon H U. Viable neutrophils release mitochondrial DNA to form neutrophil extracellular traps. *Cell Death Differ* 2009; 16:1438-1444.
7. Yousefi S, Gold J A, Andina N, Lee J J, Kelly A M, Kozlowski E, et al. Catapult-like release of mitochondrial DNA by eosinophils contributes to antibacterial defense. *Nat Med* 2008; 14:949-953.
8. Kallenberg C G, Heeringa P, Stegeman C A. Mechanisms of Disease: pathogenesis and treatment of ANCA-associated vasculitides. *Nat Clin Pract Rheumatol* 2006; 2:661-670.
9. Gupta A K, Joshi M B, Philippova M, Erne P, Hasler P, Hahn S, et al. Activated endothelial cells induce neutrophil extracellular traps and are susceptible to NETosis-mediated cell death. *FEBS Lett* 2010; 584:3193-3197.
10. Zycinska K, Wardyn K A, Zielonka T M, Demkow U, Traburzynski M S. Chronic crusting, nasal carriage of *Staphylococcus aureus* and relapse rate in pulmonary Wegener's granulomatosis. *J Physiol Pharmacol* 2008; 59 Suppl 6:825-831.
11. Popa E R, Stegeman C A, Abdulahad W H, van der Meer B, Arends J, Manson W M, et al. Staphylococcal toxic-shock-syndrome-toxin-1 as a risk factor for disease relapse in Wegener's granulomatosis. *Rheumatology (Oxford)* 2007; 46:1029-1033.
12. Stegeman C A, Tervaert J W, Sluiter W J, Manson W L, de Jong P E, Kallenberg C G. Association of chronic nasal carriage of *Staphylococcus aureus* and higher relapse rates in Wegener granulomatosis. *Ann Intern Med* 1994; 120:12-17.
13. Fuchs T A, Abed U, Goosmann C, Hurwitz R, Schulze I, Wahn V, et al. Novel cell death program leads to neutrophil extracellular traps. *J Cell Biol* 2007; 176: 231-241.
14. Kessenbrock K, Krumbholz M, Schonermarck U, Back W, Gross W L, Werb Z, et al. Netting neutrophils in autoimmune small-vessel vasculitis. *Nat Med* 2009; 15:623-625.
15. Watts R, Lane S, Hanslik T, Hauser T, Hellmich B, Koldingsnes W, et al. Development and validation of a 15. consensus methodology for the classification of the ANCA-associated vasculitides and polyarteritis nodosa for epidemiological studies. *Ann Rheum Dis* 2007; 66:222-227.
16. Margraf S, Logters T, Reipen J, Altrichter J, Scholz M, Windolf J. Neutrophil-derived circulating free DNA (cf-DNA/NETs): a potential prognostic marker for posttraumatic development of inflammatory second hit and sepsis. *Shock* 2008; 30:352-358.
17. Lögters T, Paunel-Gorgulu A, Zilkens C, Altrichter J, Scholz M, Thelen S, et al. Diagnostic accuracy of neutrophil-derived circulating free DNA (cf-DNA/NETs) for septic arthritis. *J Orthop Res* 2009; 27:1401-1407.
18. Mukhtyar C, Lee R, Brown D, Carruthers D, Dasgupta B, Dubey S, et al. Modification and validation of the Birmingham Vasculitis Activity Score (version 3). *Ann Rheum Dis* 2009; 68:1827-1832.
19. Suppiah R, Mukhtyar C, Flossmann O, Alberici F, Baslund B, Batra R, et al. A cross-sectional study of the Birmingham Vasculitis Activity Score version 3 in systemic vasculitis. *Rheumatology (Oxford)* 2010.
20. Setzer B, Schlesier M, Walker U A. Effects of didanosine-related depletion of mtDNA in human T lymphocytes. *J Infect Dis* 2005; 191:848-855.
21. Uehara A, Sato T, Iwashiro A, Yokota S. PR3-ANCA in Wegener's granulomatosis prime human mononuclear cells for enhanced activation via TLRs and NOD1/2. *Diagn Pathol* 2009; 4:23.
22. Pfister H, Ollert M, Frohlich L F, Quintanilla-Martinez L, Colby T V, Specks U, et al. Antineutrophil cytoplasmic autoantibodies against the murine homolog of proteinase 3 (Wegener autoantigen) are pathogenic in vivo. *Blood* 2004; 104:1411-1418.
23. Collins L V, Hajizadeh S, Holme E, Jonsson I M, Tarkowski A. Endogenously oxidized mitochondrial DNA induces in vivo and in vitro inflammatory responses. *J Leukoc Biol* 2004; 75:995-1000.
24. Pilsczek F H, Salina D, Poon K K, Fahey C, Yipp B G, Sibley C D, et al. A novel mechanism of rapid nuclear neutrophil extracellular trap formation in response to *Staphylococcus aureus*. *J Immunol* 2010; 185:7413-7425.
25. Xiao H, Heeringa P, Liu Z, Huugen D, Hu P, Maeda N, et al. The role of neutrophils in the induction of glomerulonephritis by anti-myeloperoxidase antibodies. *Am J Pathol* 2005; 167:39-45.
26. Tomasson G, Lavalley M, Tanriverdi K, Finkielman J D, Davis J C, Jr., Hoffman G S, et al. Relationship Between Markers of Platelet Activation and Inflammation with Disease Activity in Wegener's Granulomatosis. *J Rheumatol* 2011.
27. Tervaert J W, van der Woude F J, Fauci A S, Ambrus J L, Velosa J, Keane W F, et al. Association between active Wegener's granulomatosis and anticytoplasmic antibodies. *Arch Intern Med* 1989; 149:2461-2465.
28. Finkielman J D, Merkel P A, Schroeder D, Hoffman G S, Spiera R, St Clair E W, et al. Antiproteinase 3 antineutrophil cytoplasmic antibodies and disease activity in Wegener granulomatosis. *Ann Intern Med* 2007; 147:611-619.
29. Lee-Kirsch M A, Gong M, Chowdhury D, Senenko L, Engel K, Lee Y A, et al. Mutations in the gene encoding the 3'-5' DNA exonuclease TREX1 are associated with systemic lupus erythematosus. *Nat Genet* 2007; 39:1065-1067.
30. Hakkim A, Furnrohr B G, Amann K, Laube B, Abed U A, Brinkmann V, et al. Impairment of neutrophil extracellular trap degradation is associated with lupus nephritis. *Proc Natl Aced Sci USA* 2010; 107:9813-9818.
31. Napirei M, Karsunky H, Zevnik B, Stephan H, Mannherz H G, Moroy T. Features of systemic lupus erythematosus in Dnase1-deficient mice. *Nat Genet* 2000; 25:177-181.
32. Yasutomo K, Horiuchi T, Kagami S, Tsukamoto H, Hashimura C, Urushihara M, et al. Mutation of DNASE1 in people with systemic lupus erythematosus. *Nat Genet* 2001; 28:313-314.
33. Capolunghi F, Rosado M M, Cascioli S, Girolami E, Bordasco S, Vivarelli M, et al. Pharmacological inhibition of TLR9 activation blocks autoantibody production in human B cells from SLE patients. *Rheumatology (Oxford)* 2010; 49:2281-2289.
34. Guiducci C, Tripodo C, Gong M, Sangaletti S, Colombo M P, Coffman R L, et al. Autoimmune skin inflammation is dependent on plasmacytoid dendritic cell activation by nucleic acids via TLR7 and TLR9. *J Exp Med* 2010; 207:2931-2942.
35. Garcia-Romo G S, Caielli S, Vega B, Connolly J, Allantaz F, Xu Z, et al. Netting neutrophils are major inducers of type I IFN production in pediatric systemic lupus erythematosus. *Sci Transl Med* 2011; 3:73ra20.
36. Gabrielli A, Avvedimento E V, Krieg T. Scleroderma. *N Engl J Med* 2009; 360:1989-2003.
37. Farina G A, York M R, Di M M, Collins C A, Meller S, Homey B, et al. Poly(I:C) drives type I IFN- and TGFbeta-mediated inflammation and dermal fibrosis simulating altered gene expression in systemic sclerosis. *J Invest Dermatol* 2010; 130:2583-2593.
38. Farina G, York M, Collins C, Lafyatis R. dsRNA activation of endothelin-1 and markers of vascular activation in endothelial cells and fibroblasts. *Ann Rheum Dis* 2011: 544-550.
39. Piggott K, Biousse V, Newman N J, Goronzy J J, Weyand C M. Vascular damage in giant cell arteritis. *Autoimmunity* 2009; 42:596-604.

The invention claimed is:

1. A method for diagnosing an autoimmune or autoinflammatory disease (AID) selected from the group consisting of systemic lupus erythematosus (SLE) and ANCA-associated vasculitis (AAV) in an individual suffering from the AID or suspected of suffering from the AID that presents one or more established criteria for the diagnosis and/or classification of the AID, said method comprising the steps of:
   a. determining by quantitative PCR the amount or concentration of blood plasma circulating mitochondrial nucleic acid (mtNA) in a sample comprising blood, plasma, or serum obtained from said individual using a primer pair capable of specifically amplifying a designated mitochondrion-specific nucleotide sequence, wherein said mtNA is mitochondrial DNA (mtDNA) and said quantitative PCR utilizes amplification primers capable of specifically amplifying the mitochondrial ATP-6 gene;
   b. comparing the amount or concentration of mtDNA determined in step (a) with a control amount or concentration of mtDNA associated with a healthy subject; and
   c. diagnosing said individual with the AID when (i) said measured mtDNA amount or concentration is elevated relative to said control amount or concentration.

2. The method of claim 1, wherein the sample from said individual is a plasma sample.

3. The method of claim 1, further wherein the extent of elevation of mtDNA in the sample obtained from the individual relative to the control correlates to the progression of AID in the individual.

4. The method of claim 1, wherein said AID is ANCA-associated vasculitis (AAV).

5. The method of claim 1, wherein said AID is systemic lupus erythematosus (SLE).

6. The method of claim 1, wherein the control sample associated with a healthy subject contains from about 10,000 to about 32,000 copies of mtDNA per ml plasma and the sample obtained from said individual diagnosed with an AID contains from about 250,000 to about 1,200,000 copies of mtDNA per ml plasma.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
accaatagcc ctggccgtac                                           20

```
<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ggtggcgctt ccaattaggt                                               20

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
cggggctctc cagaacatc                                                19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
atgaccttgc ccacagcct                                                19
```